(12) United States Patent
Hosokawa et al.

(10) Patent No.: US 8,425,840 B2
(45) Date of Patent: Apr. 23, 2013

(54) MICROCHIP AND BLOOD MONITORING DEVICE

(75) Inventors: Kazuya Hosokawa, Tokyo (JP); Tomoko Wada, Tokyo (JP)

(73) Assignee: Fujimori Kogyo Co., Ltd. (JP)

( * ) Notice: Subject to any disclaimer, the term of this patent is extended or adjusted under 35 U.S.C. 154(b) by 299 days.

(21) Appl. No.: 12/744,500

(22) PCT Filed: Nov. 26, 2008

(86) PCT No.: PCT/JP2008/071445
§ 371 (c)(1),
(2), (4) Date: May 25, 2010

(87) PCT Pub. No.: WO2009/069656
PCT Pub. Date: Jun. 4, 2009

(65) Prior Publication Data
US 2010/0267066 A1   Oct. 21, 2010

(30) Foreign Application Priority Data

Nov. 26, 2007   (JP) .................................. 2007-304981
Jul. 9, 2008   (JP) .................................. 2008-179500

(51) Int. Cl.
*G01N 33/00*   (2006.01)
(52) U.S. Cl.
USPC ........... 422/68.1; 422/407; 422/502; 422/503
(58) Field of Classification Search ................. 422/68.1, 422/407, 502, 503
See application file for complete search history.

(56) References Cited

U.S. PATENT DOCUMENTS

| | | |
|---|---|---|
| 4,756,884 A | 7/1988 | Hillman et al. |
| 4,948,961 A | 8/1990 | Hillman et al. |
| 4,963,498 A | 10/1990 | Hillman et al. |
| 5,004,923 A | 4/1991 | Hillman et al. |
| 5,039,617 A | 8/1991 | McDonald et al. |
| 5,140,161 A | 8/1992 | Hillman et al. |
| 5,144,139 A | 9/1992 | Hillman et al. |
| 5,164,598 A | 11/1992 | Hillman et al. |

(Continued)

FOREIGN PATENT DOCUMENTS

| | | |
|---|---|---|
| JP | 2001252897 | 9/2001 |
| JP | 2002-277479 | 9/2002 |

(Continued)

OTHER PUBLICATIONS

Grabowski, Eric F. "Platelet Aggregation in Flowing Blood at a Site of Injury to an Endothelial Cell Monolayer: Quantitation and Real-Time Imaging with the TAB Monoclonal Antibody", Blood Jan. 15, 1990, vol. 75, No. 2; 390-398.

(Continued)

*Primary Examiner* — Sam P Siefke
(74) *Attorney, Agent, or Firm* — Kilpatrick Townsend & Stockton LLP

(57) ABSTRACT

A microchip comprising therein a first channel which allows inflow of a first liquid selected from whole blood, platelet-rich plasma and a drug-treated liquid thereof, a second channel connected to the first channel, which allows inflow of a second liquid containing an agent that is reactive with the first liquid, and a merged channel extended from the connection portion of the first channel with the second channel, wherein, in the merged channel, a stirring section having a stirring bar for mixing the first liquid with the second liquid is provided; and a blood monitoring device using the same.

10 Claims, 12 Drawing Sheets

U.S. PATENT DOCUMENTS

| | | | |
|---|---|---|---|
| 5,204,525 | A | 4/1993 | Hillman et al. |
| 5,290,692 | A | 3/1994 | Suzuki et al. |
| 5,300,779 | A | 4/1994 | Hillman et al. |
| 2004/0011413 | A1 | 1/2004 | Fujii et al. |
| 2007/0092399 | A1 | 4/2007 | Yokomine |
| 2007/0254325 | A1 | 11/2007 | Rechner |
| 2009/0311675 | A1 | 12/2009 | Hosokawa |

FOREIGN PATENT DOCUMENTS

| | | |
|---|---|---|
| JP | 2004-257766 | 9/2004 |
| JP | 2004251630 | 9/2004 |
| JP | 2005-034129 | 2/2005 |
| JP | 2005-134351 | 5/2005 |
| JP | 2006205080 | 8/2006 |
| JP | 2007024522 | 2/2007 |
| JP | 2007-147602 | 6/2007 |
| JP | 2007-298511 | 11/2007 |
| JP | 2009-068874 | 4/2009 |
| JP | 2009-223142 | 10/2009 |
| WO | WO-2007046450 | 10/2006 |
| WO | WO-2007132481 | 11/2007 |

OTHER PUBLICATIONS

Tsuji, Shizuko et al., "Real-Time Analysis of Mural Thrombus Formation in Various Platelet Aggregation Disorders: Distinct Shear-Dependent Roles of Platelet Receptors and Adhesive Proteins Under Flow", Blood Aug. 1, 1999, vol. 94, No. 3; 968-975.

Yamada, H. et al., "Laser Kako no Medical eno Oyo no Kanosei—Ketsueki Kensayo Micro Ryutai Device no Sakusei-," Laser Kyokaishi, Vo. 32, No. 1, pp. 16-24, Jan. 31, 2007.

PCT/JP2008/071445, International Search Report, Feb. 2, 2009.

"Supplemental Search Report", Application No. PCT/JP2008071445.

PCT/JP2011/052901 , "International Search Report", International Patent Application No. PCT/JP2011/052901, International Search Report mailed Mar. 15, 2011 (2 pages), Mar. 15, 2011, 2.

Fig.1
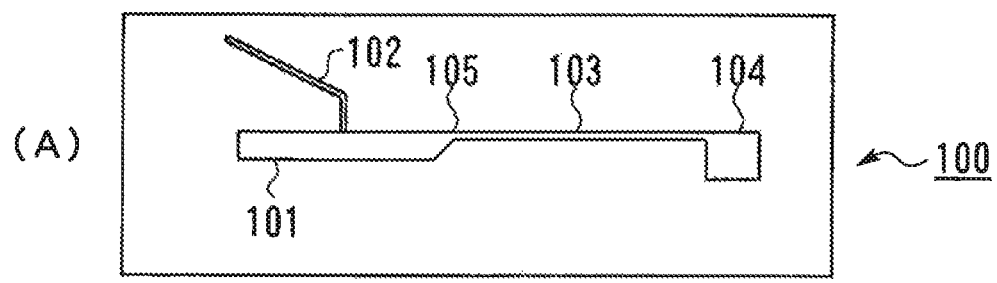
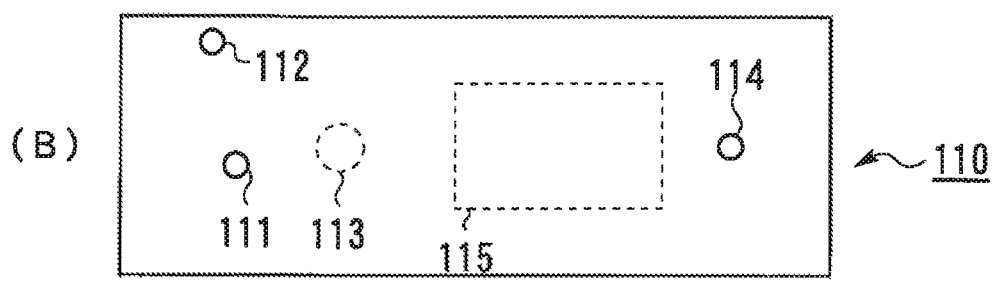
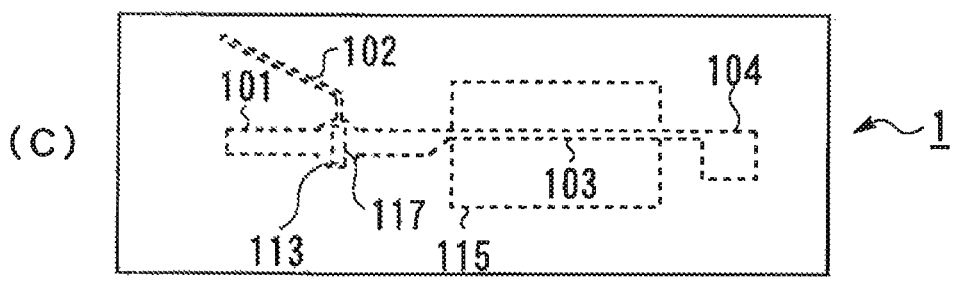
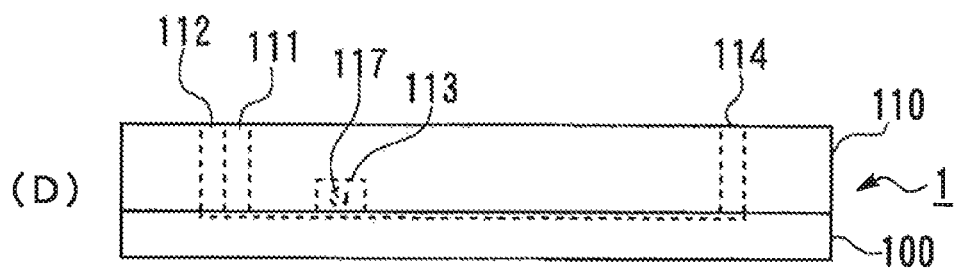

Fig.7
(A)
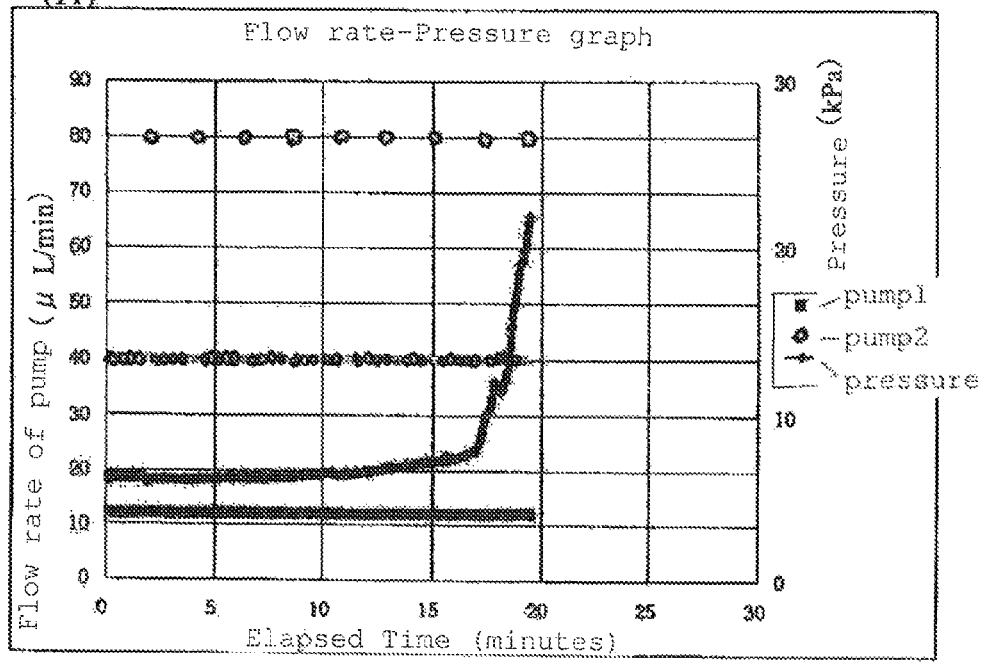
(B)
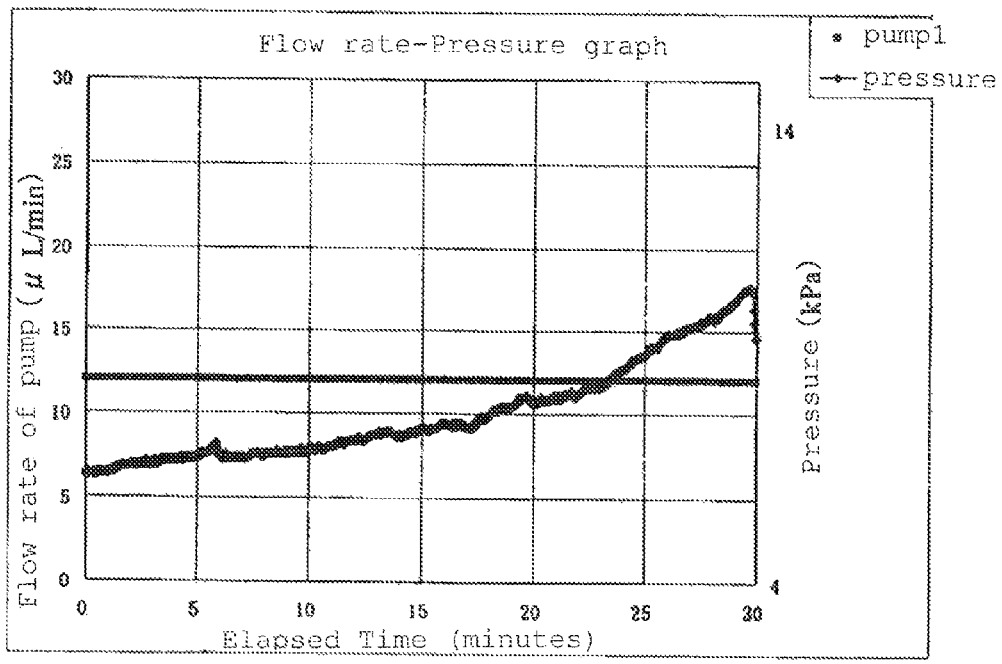

Fig.8
after 1 minute
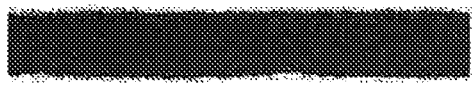
after 2 minutes
after 3 minutes
after 5 minutes

Fig.13
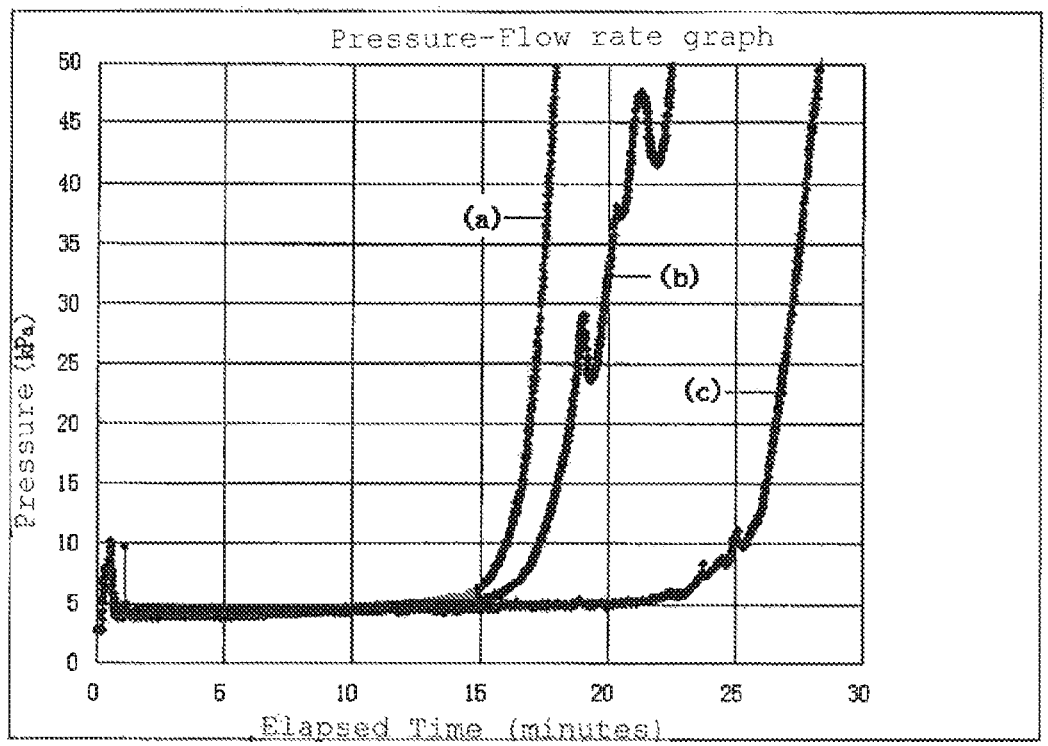
Fig.14 Thrombus formation observed with driven CCD camera
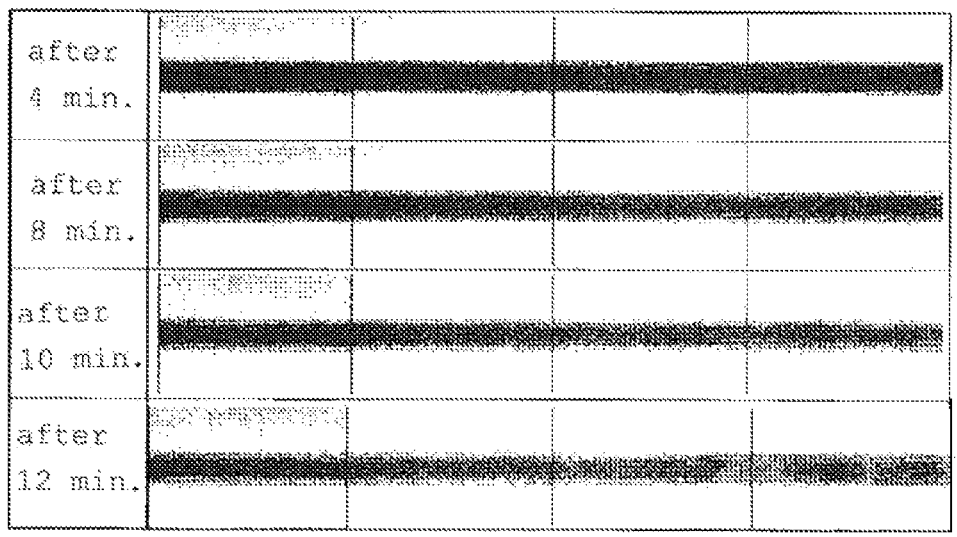

Fig.15
(A)
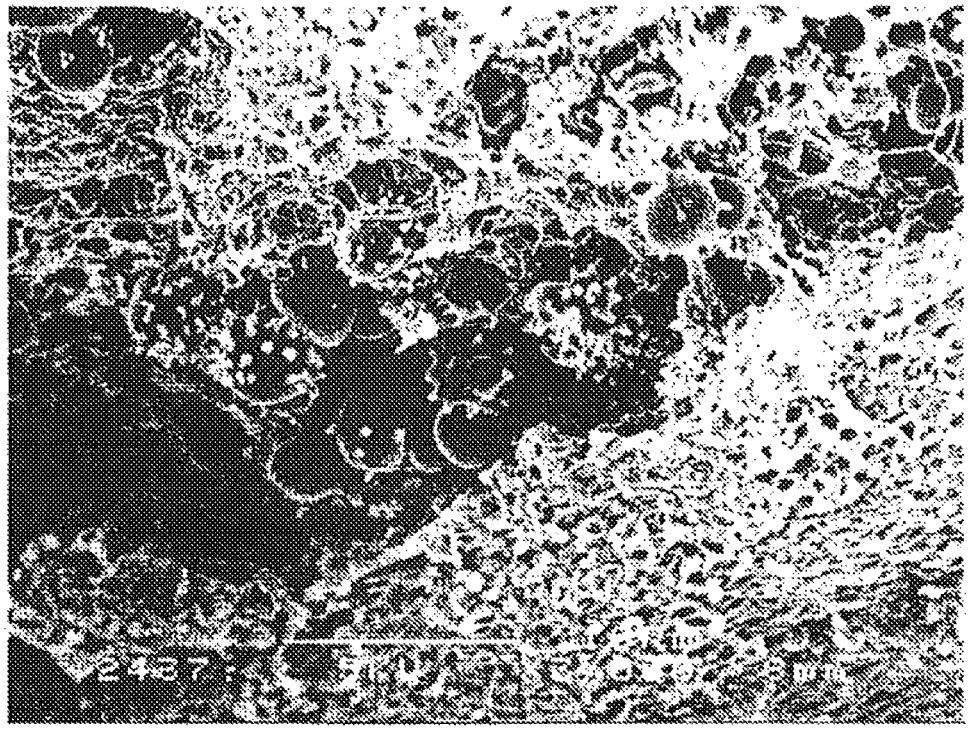
(B)
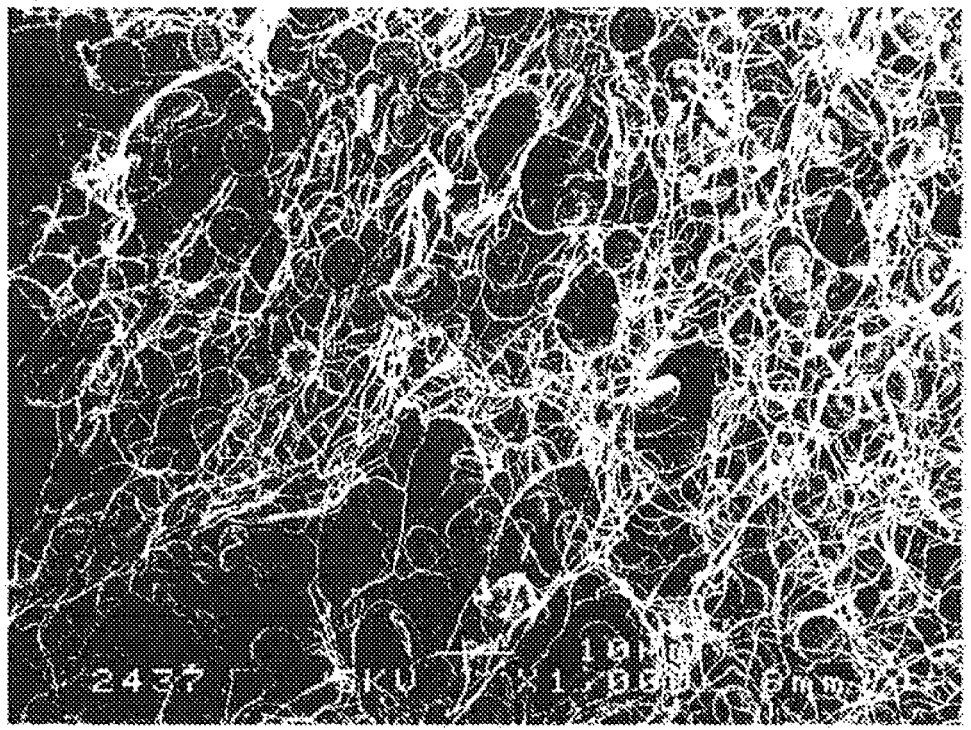

MICROCHIP AND BLOOD MONITORING DEVICE

CROSS REFERENCE TO RELATED APPLICATIONS

This application is a PCT national phase filing of International application Serial No. PCT/JP2008/071445 filed Nov. 26, 2008 and claims priority to Japanese patent application Serial No. 2007-304981 filed Nov. 26, 2007 and claims priority to Japanese patent application Serial No. 2008-179500 filed Jul. 9, 2008, the contents of all of which are incorporated herein by reference.

TECHNICAL FIELD

The present invention relates to a chip for efficiently mixing a small amount of blood with an agent to analyze the reactivity and properties of the blood, more particularly, a microchip for blood monitoring such as monitoring of blood coagulation capacity and platelet function, and a blood monitoring device using it.

BACKGROUND ART

In atherothrombosis such as myocardial infarction, atherosclerotic plaque collapses at the site of arteriosclerosis, and platelets adhere to collagen containing tissue factor which was exposed to the blood flow, followed by complex occurrence of platelet aggregation and activation of the blood coagulation system, leading to formation of a serious occlusive thrombus. Heart diseases such as myocardial infarction are serious diseases which represent the second commonest cause of death among all of the causes of death in Japan.

However, in myocardial infarction and the like, formation of a thrombus proceeds only in areas of arteriosclerosis, and the thrombotic tendency does not extremely proceed throughout the body. In vitro tests are not suited for evaluation of the thrombotic tendency in such thrombosis or for monitoring of the antithrombotic effect in antithrombotic therapy, so that a comprehensive evaluation of coagulation and platelets (adhesion and aggregation) under blood flow is important.

Conventionally, blood coagulation capacity has been evaluated by monitoring activated partial thromboplastin time (APTT) and thromboplastin time (PT) using blood plasma. Mainly, APTT reflects intrinsic coagulation and PT reflects extrinsic coagulation. As monitoring of platelets, by using platelet-rich plasma and by adding a platelet-activating substance such as adenosine diphosphate (ADP) or collagen, the aggregation capacity of the platelets can also be evaluated based on a change in transmittancy or the like. Further, coagulation time of whole blood is also measured based on whole blood coagulation time, whole blood coagulation time on recalcification or the like.

Further, as a monitoring system using whole blood, thromboelastogram is used to monitor activation of coagulation components, aggregation of platelets and the like.

However, a thrombus grows under blood flow in vivo, and since the above-described monitoring method and the like are those carried out in a closed in vitro system, it is impossible to observe a state wherein a thrombus grows in vivo.

As proposals to solve this problem, Patent Literature 1 and Non-patent Literatures 1 and 2 disclose methods for monitoring adhesion and aggregation of platelets by a confocal microscope, the method comprising allowing blood to pass through on a collagen cell, to which blood an antithrombotic agent to be evaluated was added, and fluorescently labeling the platelets.

However, since, in the inventions described in these literatures, monitoring is carried out in the presence of an anticoagulant, absence of formation of a thrombus by adhesion or aggregation of platelets induced by the coagulation system, or decreased ability of thrombus formation is evaluated by monitoring of changes in the morphology of platelets, so that activation of platelets coupled with the coagulation system is not reflected. Therefore, they are inventions preferred for evaluation of pharmacological effects of antiplatelet drugs, but incapable of monitoring a thrombus itself or the entire process of thrombus formation.

Further, in Patent Literature 2, disclosed is a thrombus monitoring device for monitoring thrombus formation by allowing anticoagulated blood to flow into a channel mimicking a blood vessel while releasing the anticoagulation treatment or promoting blood coagulation, the device comprising: a thrombus formation chamber which has been provided with, in at least a part of the inside thereof, a thrombus-inducing material that induces formation of a thrombus; an inlet tube connected to the thrombus formation chamber, for allowing blood to inflow into the thrombus formation chamber; and an agent tube connected to the inlet tube, for feeding into the inlet tube an agent for releasing the anticoagulation treatment or an agent for promoting blood coagulation. By this device, monitoring of blood can be carried out by using a small amount of a blood sample, but there were cases where the blood and the agent for releasing the anticoagulation treatment or the agent for promoting blood coagulation could not be mixed well, so that there was a room for improvement.

Further, in cases where platelets were stained with quinacrine by the method according to Patent Literature 1 or Non-patent Literature 1 or 2, leukocytes were also stained at the same time, so that selective evaluation of only the function of platelets was impossible. Further, there were many points unsuitable for the monitoring, such as color deterioration of the fluorescent dye and expensiveness of the device.

Further, in a conventional evaluation of fibrinolytic capacity, only lysis of fibrin is measured, and there has been no method capable of measuring the lytic effect on a white thrombus formed in an actual artery.

Microfluidic chips formed by engraving a groove to provide a desired channel on a substrate and laminating the substrate with a cover plate are used in a wide variety of uses such as capillary electrophoresis and PCR as well as various monitoring. Since a liquid in a microchip forms a laminar flow due to a very large Reynolds number, it is difficult to mix the liquid in the microchip naturally. To solve this problem, various approaches have been taken.

For example, a stirring bar consisting of a columnar projection is proposed in Patent Literature 3; a stirring bar which vibrates by the piezoelectric effect is proposed in Patent Literature 4; and a stirring bar which rotates by light pressure is proposed in Patent Literature 5. However, in some cases, when a liquid containing whole blood, platelet-rich plasma or a drug-treated liquid thereof is stirred in a microchip using the proposed stirring bars, activation occurs leading to blood coagulation or the like, so that, for example, in cases where blood coagulation, the function of platelets or the like is monitored, accurate monitoring is very difficult. Further, the liquid in a microchip could be made to be naturally mixed by extending the channel, but in this case, the microchip becomes large, which is problematic. And, if the channel is made to wind a plurality of times in switchback style, activation occurs at regions where the liquid remains and the like, leading to blood coagulation or the like, so that the monitoring cannot be carried out accurately.

Patent Literature 1: JP 2004-251630 A
Patent Literature 2: WO 2007/046450
Patent Literature 3: JP 2007-24522 A
Patent Literature 4: JP 2006-205080 A
Patent Literature 5: JP 2001-252897 A
Non-patent Literature 1: Blood. 1990; 75:390-398
Non-patent Literature 2: Blood. 1999 Aug. 1; 94 (3):968-75

DISCLOSURE OF THE INVENTION

The present invention was made in view of the above-described circumstances and aims to provide a device and a method by which thrombus formation by blood coagulation and platelets can be efficiently and accurately evaluated under circumstances equivalent to those in blood flow using a small amount of whole blood or platelet-rich plasma (these may be collectively referred to as "blood" in the present specification).

To solve the problems, the present invention provides a microchip comprising therein: a first channel which allows inflow of a first liquid selected from whole blood, platelet-rich plasma and a drug-treated liquid thereof, a second channel connected to the first channel, which allows inflow of a second liquid containing an agent that is reactive with the first liquid, and a merged channel extended from the connection portion of the first channel with the second channel, wherein, in the merged channel, a stirring section having a stirring bar for mixing the first liquid with the second liquid is provided.

The surface of the stirring bar has been preferably subjected to coagulation inhibition treatment. Here, the coagulation inhibition treatment is not restricted as long as it does not activate the contacting layer of the coagulation system, and preferably a treatment by which at least the surface of the stirring bar is formed with heparin, polyvinyl lactonamide or poly(2-methoxyethyl acrylate).

Preferably, in the microchip of the present invention, the width of the stirring section is larger than that of the merged channel and gradually decreases in the direction toward the downstream.

Further, preferably, the depth of the stirring section is larger than that of the merged channel and gradually decreases in the direction toward the downstream.

In the microchip of the present invention, the depth of the merged channel is preferably 50 μm to 200 μm.

The microchip of the present invention is preferably a microchip constituted by laminating a first substrate having a groove engraved on the surface, which groove constitutes the first channel, second channel and merged channel, and a second substrate having a hole engraved on the surface, which hole corresponds to the stirring section, such that the opening sections of the groove and hole are facing inward. Here, preferably, the bonding strength between the first substrate and the second substrate is 0.5 to 50 kgf, and the pressure resistance is 100 kPa when blood is allowed to flow therein.

The microchip of the present invention preferably has, in the downstream of the stirring section, a thrombus formation chamber which has been provided with, in at least a part of the inside thereof, a thrombus formation-inducing material which induces formation of a thrombus. Here, the thrombus formation-inducing material is preferably collagen or a mixture of collagen and tissue factor.

The present invention also provides a method for measuring thrombus formation using any one of the above-described microchips, the method comprising: allowing anticoagulated blood and a reagent for releasing the anticoagulation treatment to inflow from the first channel and the second channel, respectively, into the stirring section; mixing the anticoagulated blood and the reagent for releasing the anticoagulation treatment in the stirring section; and thereafter measuring thrombus formation in the thrombus formation chamber. Here, preferably, the anticoagulated blood is blood anticoagulated with citric acid and the reagent for releasing the anticoagulation treatment is a solution containing calcium.

The present invention also provides a method for measuring thrombus formation and thrombolysis using any one of the above-described microchips, the method comprising: allowing anticoagulated blood and a reagent for releasing the anticoagulation treatment to inflow from the first channel and the second channel, respectively, into the stirring section; mixing the anticoagulated blood and the reagent for releasing the anticoagulation treatment in the stirring section; thereafter measuring thrombus formation in the thrombus formation chamber; and further lysing the formed thrombus by allowing a thrombolytic substance to inflow from the second channel. Here, the thrombolytic substance is preferably one or more selected from the group consisting of plasmin, urokinase and tissue plasminogen activator.

The present invention also provides a method for measuring platelet function using any one of the above-described microchips, the method comprising: allowing anticoagulated blood and a reagent for activating platelets to inflow from the first channel and the second channel, respectively, into the stirring section; mixing the anticoagulated blood and the reagent for activating platelets in the stirring section; and measuring platelet function by allowing the resulting mixture to pass through the thrombus formation chamber. Here, preferably, the anticoagulated blood is blood anticoagulated with citric acid or heparin and the reagent for activating platelets is ADP, collagen, ristocetin or arachidonic acid.

In each of the above-described methods, the volume ratio between the anticoagulated blood allowed to inflow from the first channel and the reagent allowed to inflow from the second channel is preferably 10:2 to 100:1. Further, in the stirring section, the mixture of the blood having inflowed from the first channel and the reagent having inflowed from the second channel is preferably stirred for 5 seconds to 3 minutes. Further, the rotation speed of the stirring bar is preferably 30 to 300 rotations/minute.

The present invention also provides a blood monitoring device comprising anyone of the above-described microchips. In the blood monitoring device of the present invention, the microchip of the present invention is preferably placed such that the first channel and the second channel are located at the lower side and the merged channel is located at the upper side.

Further, the blood monitoring device of the present invention preferably has a pressure sensor to measure the pressure (s) on at least one of the first channel, the second channel and the merged channel.

Further, the blood monitoring device of the present invention preferably has a camera to observe the inside of the merged channel.

The camera preferably has a function to automatically take still images or moving images of the inside of the channel at constant intervals. More preferably, the camera can take still images of the entire channel as a panoramic photograph or a sequence of still images at constant intervals, thereby enabling visual confirmation of the state of obstruction of the channel after the measurement.

The present invention also provides a method for monitoring of blood using the microchip of the present invention, the method comprising; mixing anticoagulated whole blood or platelet-rich plasma with an agent for releasing the anticoagulation treatment, an agent for activating platelets or a thrombolytic agent by stirring in a channel; and monitoring by allowing them to flow in the channel. Here, the thrombolytic agent is preferably at least one selected from urokinase, plasmin and tissue plasminogen activator (tPA). The method for monitoring of blood is preferably a method for measuring blood coagulation or platelet function. The agent for activating platelets is preferably at least one selected from adenosine diphosphate (ADP), collagen, thrombin and ristocetin. The method of the present invention for monitoring of blood is preferably used for monitoring of blood coagulation or platelet function.

BRIEF DESCRIPTION OF THE DRAWINGS

FIG. 1 is a conceptual diagram showing important parts of the microchip 1 according to the first embodiment of the present invention. (A) shows the first substrate of the microchip 1; (B) shows the second substrate of the microchip 1; (C) shows a plan view of a completed microchip 1; and (D) shows a front view of a completed microchip 1 (the stirring bar is not shown).

FIG. 7 shows graphs of the flow rate-pressure observed when the blood monitoring device A of the present invention was used. (A) shows results obtained when whole blood, to which 1/10 volume of 3.2% sodium citrate was added and further to which a corn-derived trypsin inhibitor was added to a final concentration of 25 μg/ml, was allowed to inflow from the first pump; 0.2 M $CaCl_2$ was allowed to inflow from the second pump; and 0.5 M EDTA (pH 10) was allowed to inflow from the third pump. (B) shows results obtained when whole blood, to which 1/10 volume of 3.2% sodium citrate was added, was allowed to inflow from the first pump; and 0.1 μM ADP solution was allowed to inflow from the second pump.

FIG. 8 shows a diagram (photographs) showing the appearance of a thrombus observed using the blood monitoring device of the present invention B.

FIG. 13 is a graph of the flow rate-pressure observed when the blood monitoring device C of the present invention was used. (a) represents a control (Example 7), (b) represents 8,000 U/ml tPA formulation (Example 10), and (c) represents 0.5 U/ml low-molecular-weight heparin (Example 9).

FIG. 14 is a diagram (halftone pictures) produced by taking still images at each position with time using the CCD camera of the thrombus monitoring device C of the present invention and reconstructing the images.

FIG. 15 shows scanning electron micrographs of thrombi. A is a diagram showing a white thrombus observed by peeling the microchip of the thrombus monitoring device C of the present invention. B shows a blood clot formed by leaving the subject to be static.

Figure 2:
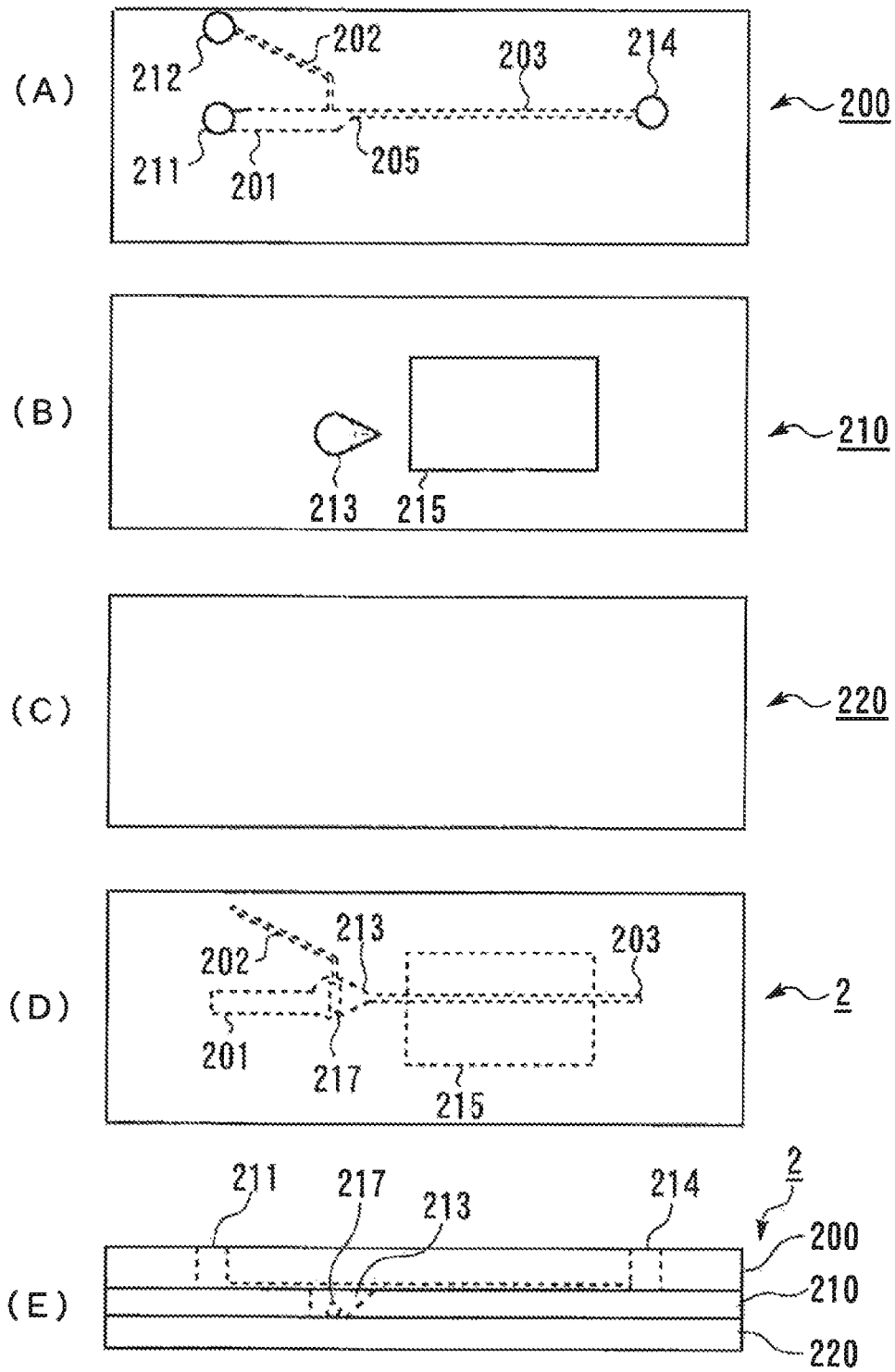
FIG. 2 is a conceptual diagram showing important parts of the microchip 2 of the second embodiment of the present invention. (A) shows the first substrate of the microchip 2; (B) shows the second substrate of the microchip 2; (C) shows the third substrate of the microchip 2; (D) shows a plan view of a completed microchip 2; and (E) shows a front view of a completed microchip 2 (the stirring bar is not shown).

| DESCRIPTION OF SYMBOLS | |
|---|---|
| 1, 2, 3, 4: | Microchip; |
| 40: | Stage; |
| 100, 200, 300, 400: | First substrate; |
| 110, 210, 310, 410: | Second substrate; |
| 220: | Third substrate; |
| 101, 201, 301, 401: | First channel; |
| 102, 202, 302, 402: | Second channel; |
| 103, 203, 303, 403: | Merged channel; |
| 104, 304: | Waste liquid reserving section; |
| 105, 205, 305: | Narrowing section; |
| 111, 211, 311, 411: | First inlet; |
| 112, 212, 312, 412: | Second inlet; |
| 113, 213, 313, 413: | Stirring section; |
| 114, 214, 314, 414: | Outlet; |
| 115, 215, 315, 415: | Inducing material-placing section (thrombus formation chamber); |
| 117, 217, 317, 417: | Stirring bar; |
| 306, 406: | Third channel; |
| 318, 418: | Third inlet; |
| 320, 420: | First pump (pump 1); |
| 321, 421: | Second pump (pump 2); |
| 322, 422: | Third pump (pump 3); |
| 323: | Fixation hole; |
| 324, 424: | Camera; |
| 325, 425: | Image analyzer; |
| 326: | Microchip-fixing pin; |
| 327, 427: | Heater; |
| 328: | Monitoring slit; |
| 329, 429: | Stirrer; |
| 330: | Microchip-placing stage; |
| 331, 431: | Illumination; |
| 432: | Pressure sensor; |
| 433: | Blood reservoir; |
| 434: | Waste liquid tank; |
| 435: | First connection nozzle; |
| 436: | Second connection nozzle; |
| 437: | Waste liquid tube; |
| A: | Blood monitoring device; |
| B: | Blood monitoring device; |
| C: | Blood monitoring device. |

EFFECT OF THE INVENTION

In the microchip of the present invention, inclusion of a stirring bar for mixing the first liquid and the second liquid in the merged channel allows stirring and mixing uniformly the first liquid and the second liquid in the mixing section of the microchip while suppressing activation of blood coagulation which leads to occurrence of a blood coagulation clot or the like, so that the microchip of the present invention according to claim 1 is suitable for monitoring, for example, blood coagulation and platelet function using a liquid containing whole blood, platelet-rich plasma or a drug-treated liquid thereof or the like.

In the microchips of the present invention in cases where the coagulation inhibition treatment for inhibiting coagulation of the liquid produced by confluence of the first liquid and the second liquid is a treatment by which at least the surface of the stirring bar is formed with heparin, polyvinyl lactonamide or poly(2-methoxyethyl acrylate), the stirring bar can be prepared by coating by soaking in a molten resin or resin finishing such as injection molding, and therefore the microchips can be efficiently prepared.

In the microchip of the present invention, since the width of the stirring section is larger than that of the merged channel, the liquid produced by confluence of the first liquid and the second liquid can be made to stay in the stirring section longer, so that sufficient stirring can be attained.

In the microchip of the present invention, since the width of the stirring section gradually decreases in the direction toward the downstream, the mixed solution after the stirring smoothly flows into the merged channel in the downstream, so that activation of the liquid, which leads to blood coagulation and the like, does not occur at the outlet of the stirring section. Further, since the air in the stirring section easily flows out, the air does not remain in the stirring section.

In the microchip of the present invention, since the depth of the stirring section is larger than that of the merged channel, the liquid produced by confluence of the first liquid and the second liquid can be made to stay in the stirring section longer, so that sufficient stirring can be attained.

In the microchip of the present invention since the depth of the stirring section decreases in the direction toward the downstream, the mixed solution containing blood after the stirring smoothly flows into the merged channel in the downstream, so that the activation of the liquid, which leads to blood coagulation and the like, does not occur at the outlet of the stirring section. Further, since the air in the stirring section easily flows out, the air does not remain in the stirring section.

In the microchip of the present invention, since the depth of the merged channel is 50 μm to 200 μm analysis can be carried out with small amounts of sample and reagents, which is preferred.

In the microchip of the present invention, since the microchip can be obtained by laminating: a first substrate having a groove engraved on the surface, the groove constituting the first channel, second channel and merged channel; and a second substrate having a hole engraved on the surface, the hole corresponding to the stirring section; with each other such that the opening sections of the groove and hole are facing inward, the microchip can be easily prepared.

In the microchip of the present invention, since the bonding strength of the first substrate with the second substrate is 0.5 to 50 kgf, analysis can be carried out, after measuring thrombus formation, by peeling the both substrates, which is preferred.

Further, in the microchip of the present invention, since the microchip has a thrombus formation chamber in the downstream of the stirring section, which chamber has been provided with, in at least a part of the inside thereof, a thrombus formation-inducing material which induces formation of a thrombus, thrombus formation is induced when the stirred mixed solution passes through the thrombus formation chamber, so that a thrombus due to the blood coagulation capacity or platelets can be allowed to form.

In the microchip of the present invention, since the thrombus formation-inducing material is collagen or a mixture of collagen and tissue factor, the thrombus can be allowed to form efficiently.

In the measurement method of the present invention, since anticoagulated blood and a reagent for releasing the anticoagulation treatment are allowed to inflow from the first channel and the second channel, respectively, into the stirring section and mixed in the stirring section, followed by measurement of thrombus formation in the thrombus formation chamber, the blood and the reagent are mixed efficiently and reaches the thrombus formation chamber, so that thrombus formation can be measured efficiently.

In the measurement method of the present invention, since the anticoagulated blood is blood anticoagulated with citric acid and the reagent for releasing the anticoagulation treatment is a solution containing calcium, the anticoagulation treatment can be carried out inexpensively, which is preferred.

In the measurement method of the present invention, since anticoagulated blood and a reagent for releasing the anticoagulation treatment are allowed to inflow from the first channel and the second channel, respectively, into the stirring section and mixed in the stirring section, followed by measurement of thrombus formation in the thrombus formation chamber, and lysing the formed thrombus by allowing a thrombolytic substance to inflow from the second channel, so that both thrombus formation and thrombolysis can be measured.

In the measurement method of the present invention, since the thrombolytic substance is at least one selected form the group consisting of plasmin, urokinase and tissue plasminogen activator, the thrombus can be lysed efficiently.

In the measurement method using the microchip of the present invention, platelet function can be measured by allowing anticoagulated blood and a reagent for activating platelets to inflow from the first channel and the second channel, respectively, into the stirring section, mixing the anticoagulated blood and the reagent for activating platelets in the stirring section, and thereafter allowing the resulting mixture to pass through the thrombus formation chamber.

In the measurement method of the present invention, since the anticoagulated blood is blood anticoagulated with citric acid or heparin and the reagent for activating platelets is ADP, collagen, ristocetin or arachidonic acid, platelets can be activated efficiently.

In the measurement method of the present invention, since the volume ratio between the anticoagulated blood allowed to inflow from the first channel and the reagent allowed to inflow from the second channel is 10:2 to 100:1, thrombus formation, thrombolysis or activation of platelets can be efficiently caused with a small amount of the reagent.

In the measurement method of the present invention, since, in the stirring section, the mixture of the blood having inflowed from the first channel and the reagent having inflowed from the second channel is stirred for 5 seconds to 3 minutes, the blood and the reagent can be mixed uniformly.

In the measurement method of the present invention, since the rotation speed of the stirring bar is 30 to 300 rotations/minute, the stirring can be carried out under a gentle condition.

Since the blood monitoring device of the present invention comprises the microchip of the present invention, monitoring of blood can be carried out efficiently with a small amount of a blood sample, so that the burden of the subject can be small.

Further, in the blood monitoring device of the present invention, if the microchip is placed such that the first channel and the second channel are located in the lower side and the merged channel is located in the upper side, in the case of occurrence of bubbles in a channel or the stirring section, the bubbles are naturally expelled to the upper side and the stirring and mixing can be carried out stably and uniformly without being disturbed by the bubbles, so that monitoring of blood can be accurately carried out.

Further, if the first channel, the second channel and the merged channel are placed in the upper side and the groove for stirring containing the stirring bar is placed in the lower side, stirring and mixing can be carried out uniformly without remaining of bubbles in the stirring section, so that monitoring of blood can be accurately carried out.

Further, if the blood monitoring device of the present invention has a pressure sensor to measure the pressure(s) on at least one of the first channel, the second channel and the merged channel, the extents of thrombus formation and thrombolysis can be expressed in values, so that quantitative evaluation can be carried out.

Further, if the blood monitoring device of the present invention has a camera for observation of the inside of the merged channel, processes of thrombus formation and thrombolysis can be visually observed.

The camera to be placed is preferably capable of taking still images or moving images. If the camera can automatically take and store still or moving images of the inside at constant intervals, the state wherein thrombus is forming can be visually evaluated with time after the measurement, which is preferred. If images of the inside of the entire channel can be taken as a panoramic photograph or a sequence of still images, storage of, and comparison among these can be simply carried out, which is more desirable. When the still or moving images are taken, installation of a transmissive light source, that is, a light source in the opposite side of the camera enables to take clearer images.

The thrombus formed in the microchip is recovered after the measurement and its shape, composition or the like is investigated depending on the purpose under a microscope using an electron microscope or fluorescent staining, or by electrophoresis, thereby enabling more detailed examinations. If the chip of the area coated with the thrombus-inducing material can be easily peeled by hand, the thrombus can be recovered from the inside after the measurement, which is desirable.

Since, in the blood monitoring method of the present invention, anticoagulated whole blood or platelet-rich plasma is mixed by stirring with an agent for releasing the anticoagulation treatment, an agent for activating platelets or a thrombolytic agent in a channel and monitored while being allowed to flow in the channel using the microchip of the present invention, it is possible to monitor the efficacy of an anti-thrombotic agent or the like in an environment similar to that in the human body, to measure platelet functions such as adhesion and aggregation of platelets, to monitor thrombolysis by confirmation of changes in the size of a thrombus, and the like.

If the thrombolytic agent is at least one selected from urokinase, plasmin and tPA, thrombolysis of a formed thrombus can be efficiently monitored under an environment similar to the physiological state. Further, if the agent for activating platelets is at least one selected from ADP, collagen, thrombin and ristocetin, platelets can be efficiently activated.

Further, if the above-described method is a method for investigating the blood coagulation capacity or platelet function, the efficacy of an antithrombotic agent and function of platelets in blood can be investigated, which is preferred.

BEST MODE FOR CARRYING OUT THE INVENTION

First, the microchip of the present invention will be described referring to drawings.

FIG. 1 is a conceptual diagram showing the first embodiment of the microchip of the present invention. The first embodiment will now be described based on FIG. 1.

FIG. 1A is a plan view of a first substrate 100 having a groove engraved on the surface, which groove constitutes the channels of the microchip. FIG. 1B is a plan view of a second substrate 110 having a hole engraved on the back side, which hole constitutes the section wherein the stirring bar of the microchip is placed. FIGS. 1C and D show a plan view and a front view of the microchip 1 of the first embodiment, wherein the first substrate 100 and the second substrate 110 are laminated with each other such that the opening sections of the groove and hole are facing inward. Each dashed line indicates that a groove, hole or the like exists in the inside of the microchip 1.

In FIG. 1A, on the first substrate 100, a single continuous groove is provided as the first channel 101 and the merged channel 103. This groove has the narrowing section 105 in the middle, and in the upstream of the narrowing section 105, the second channel 102 connected to a portion where the width of the groove is large is provided. The cross-sectional shapes of these grooves are arbitrary and each groove may be rectangular, U-shaped, V-shaped or the like. At the downstream end of the merged channel 103, a hole corresponding to the waste liquid reserving section 104 is provided. The aperture shape of the hole is arbitrary and may be circular, rectangular or the like, and the bottom surface may be either flat or curved. In the descriptions of the drawings of the present description, "upstream" means the left side of each drawing and "downstream" means the right side of each drawing.

In FIG. 1B, on the second substrate 110, a penetrating hole constituting the first inlet 111 at the position corresponding to the starting end in the upstream of the first channel 101; a penetrating hole constituting the second inlet 112 at the position corresponding to the starting end in the upstream of the second channel 102 on the first substrate 100; a penetrating hole constituting the outlet 114 at the position corresponding to the waste liquid reserving section 104 on the first substrate 100; and a cylindrical hole constituting the stirring section 113 at the position corresponding to the connection portion of the first channel 101 with the second channel 102 on the first substrate 100 are engraved, which correspondences are expected when the second substrate 110 is laminated with the first substrate 100. The bottom surface of each hole may be either flat or curved. Further, on the back side of the second substrate 110 which covers the area from the narrowing section 105 to the downstream merged channel 103 on the first substrate 100, a thrombus formation-inducing material such as collagen is applied. Particularly, as shown in FIG. 1C, it is applied widely to the inducing material-placing section 115 so as to have a margin of safety. The merged channel 103 which passes through the inside of the inducing material-placing section 115 works as the thrombus formation chamber.

Examples of the thrombus formation-inducing material include collagen and vWF (von Willebrand factor); thrombi prepared preliminarily; and fiber base materials such as silk and cotton. These may be used solely or in combination. Among these, collagen is especially preferred since it is easily available, easy to handle, and can be a model similar to the actual blood vessel, and the material may also be one containing collagen and tissue thromboplastin. In order to avoid flowing out of the thrombus formation-inducing material by the blood flow, the thrombus formation-inducing material such as collagen or vWF is coated on the inducing material-placing section with a high bonding strength. The coating of collagen can be easily attained with a high bonding strength, for example by a process wherein collagen is dissolved into an acidic solution and a glass or polystyrene substrate given hydrophilicity is soaked therein, followed by washing and drying of the processed substrate, as described in JP 05-260950 A and Blood. 1995 Apr. 1; 85 (7): 1826-35.

In cases where the coating is applied to a hydrophobic resin or the like, the coating can be carried out, after hydrophilization of the surface of the resin by plasma treatment or the like, by application of a collagen solution to a desired area, followed by drying the resultant in the air or under reduced pressure.

Further, the thrombus formation-inducing material such as a fiber base material or thrombus prepared preliminarily is preferably fixed inside the merged channel 103 in the inducing material-placing section 115. By impregnation of collagen into a thin hygroscopic fiber base material such as cotton, non-woven fabric, woven fabric or the like and drying of the resultant, a thrombus formation-inducing material having a higher thrombus formation-inducing capacity can be obtained. Further, by soaking those base materials in a collagen solution containing tissue thromboplastin and drying of the resultant, an even higher thrombus formation-inducing capacity can be obtained.

In cases where collagen is used for the coating as a thrombus formation-inducing material, if the substrate of at least the portion of the second substrate 110 which constitutes the inducing material-placing section 115 is made of a smooth glass or plastic, an excellent adhesion of collagen can be attained, which is preferred. In cases where a plastic is used as the base material, by hydrophilization thereof by plasma treatment or the like and application of a collagen solution on the desired area using a dispenser such as a pipette or syringe, followed by drying the resultant in the air or under reduced pressure, the base material can be easily coated with collagen or collagen containing tissue thromboplastin.

The narrowing section 105 also constitutes the thrombus formation-inducing material, and in some cases, only the narrowing section 105 is used as the thrombus formation-inducing material. If the narrowing portion 105 is provided as in the present embodiment, platelet aggregation induced by high shear stress can be monitored, and thrombus formation in atherothrombosis can also be reproduced, which is preferred.

As shown in FIGS. 1C and D, the microchip 1 of the first embodiment is obtained by laminating the second substrate 110 on the first substrate 100 such that the inducing material-placing section 115 provided on the second substrate 110 faces inward and that the substrates closely contact with each other and thereby each channel and the stirring section 117 are sealed.

The material of the microchip is preferably a metal, glass, plastic, silicone or the like. In view of usage in blood monitoring (image analysis, especially), a transparent material is preferred. Further, in view of formation of a circuit, a plastic is preferred, and a transparent plastic is especially preferred. In cases where the material is a silicone such as PDMS (polydimethylsiloxane), excellent adhesion is attained between the substrates, so that the first substrate 100 can be laminated with the second substrate 110 even by pressing without using an adhesive or the like for adhesion, but in cases where a high pressure is applied to the inside of the microchip 1, an adhesive is preferably used. In cases where a substrate made of polystyrene is used, the inside of each channel can be easily coated with polyvinyl lactonamide (PVLA) with a high bonding strength. Therefore, in cases where blood that has not been anticoagulated is used, blood coagulation at unintended locations can be suppressed. Further, blood coagulation at unintended locations can be easily and efficiently suppressed also by poly(2-methoxyethyl acrylate) (PMEA). The grooves and holes provided on the substrate of the microchip 1 can be engraved with a cutter or laser beam, and in cases where the material of the microchip 1 is plastic, they can also be formed by injection molding. Formation by injection molding is preferred since microchips 1 having a constant quality can be prepared efficiently.

An example of blood monitoring using the microchip 1 of the present embodiment will now be described based on FIGS. 1C and D. To the first inlet 111 and second inlet 112, tubes not shown are connected, and via the tubes, a liquid sending pump, a vacuum blood collection tube and/or a syringe is/are connected, which is/are not shown. The blood and the agent are introduced with the connected pump, vacuum blood collection tube or syringe into the first channel 101 and second channel 102, respectively. In cases where blood that has not been anticoagulated is used, the containers such as a syringe and a vacuum blood collection tube connected to the microchip are preferably heparin-coated containers or containers coated with materials having an anticoagulating activity such as polyvinyl lactonamide (PVLA) or poly(2-methoxyethyl acrylate) (PMEA).

The blood as the first liquid, which was introduced from the first inlet 111 and passed through the first channel 101, and the second liquid containing an agent that is reactive with the blood, which liquid was introduced from the second inlet 112 and passed through the second channel 102, join together at the portion where the first channel 101 is connected with the second channel 102, reaching the stirring section 113 thereafter. In the stirring section 113, the blood is uniformly mixed with the agent by the stirring bar 117, and the resulting mixture flows down the merged channel 103 while allowing the reaction between the blood and the agent. The solution mixed by stirring passes through the narrowing section 105 of the merged channel 103 and the inducing material-placing section 115 to induce thrombus formation. In the narrowing section 105, by monitoring the flow rate or properties of the mixture that passes through the merged channel 103, monitoring of interest such as monitoring of the reactivity with blood can be carried out. The blood used for the monitoring is stored in the waste liquid reserving section 104 provided at the end of the merged channel 103, and discharged from the outlet 114 as required. Further, the blood used for the monitoring may be directly discharged from the outlet 114 without providing the waste liquid reserving section 104.

The stirring bar 117 can be preferably rotated by magnetic transmission, from the outside of the microchip, of the rotating force of the motor not shown. The stirring bar 117 is subjected to coagulation inhibition treatment for inhibiting coagulation of the liquid produced by confluence of the first liquid and the second liquid. The coagulation inhibition treatment may include a treatment for surface formation of a stirring bar by coating of the surface of a magnetic material with heparin, polyvinyl lactonamide (PVLA), poly(2-methoxyethyl acrylate) (PMEA) or the like by soaking the magnetic material in a molten resin or by resin finishing such as in-mold injection molding.

FIG. 2 is a conceptual diagram showing the second embodiment of the microchip of the present invention. The second embodiment will now be described based on FIG. 2. The difference of the present embodiment from the first embodiment is that the microchip 2 is constituted by 3 substrates. Descriptions overlapping with those of the first embodiment will be omitted.

FIG. 2A is a plan view of the first substrate 200 having: grooves engraved on the back side, which grooves constitute the channels of the microchip; and penetrating holes engraved that are connected to the grooves and constitute the inlet and outlet. FIG. 2B is a plan view of the second substrate 210 having a penetrating hole which constitutes the section wherein the stirring bar of the microchip is placed. FIG. 2C is a plan view of the third substrate 220 which constitutes the bottom of the section wherein the stirring bar is placed. FIGS. 2D and E are a plan view and a front view of the microchip 2 of the second embodiment, wherein these three substrates are laminated with each other.

In FIG. 2B, on the second substrate 210, a penetrating hole which constitutes a stirring section 213 when it is laminated is engraved. This penetrating hole has a form such that the width thereof gradually decreases in the direction toward the downstream and the depth thereof gradually decreases in the direction toward the downstream. In the present embodiment, on the surface of the second substrate 210, a thrombus formation-inducing material is provided.

As shown in FIGS. 2D and E, the microchip 2 of the second embodiment is obtained by laminating the second substrate 210 under the first substrate 200 such that these closely contact with each other to keep each channel sealed, and laminating the third substrate 220 under the second substrate 210 such that the substrates closely contact with each other, so that the third substrate 220 constitutes the bottom of the stirring section 213 provided on the second substrate 210.

Figure 3:
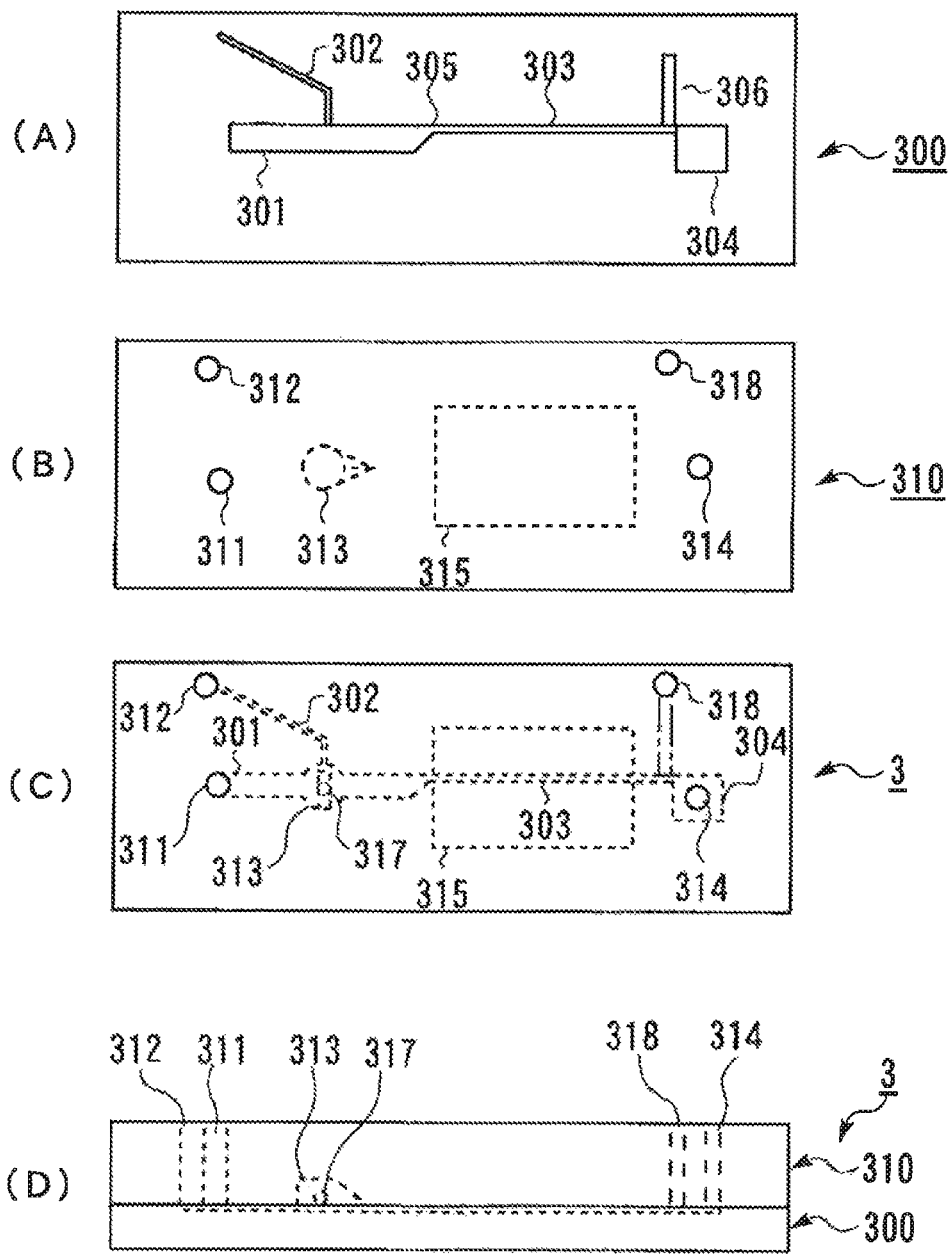
FIG. 3 is a conceptual diagram showing important parts of the microchip 3 of the third embodiment of the present invention. (A) shows the first substrate of the microchip 3; (B) shows the second substrate of the microchip 3; (C) shows a plan view of a completed microchip 3; and (D) shows a front view of a completed microchip 3 (the stirring bar is not shown).

FIG. 3 is a conceptual diagram showing the third embodiment of the microchip of the present invention. The third embodiment will now be described based on FIG. 3. The difference of the present embodiment from the first embodiment is that the microchip 3 is constituted by providing a third channel. Descriptions overlapping with those of the first embodiment will be omitted.

FIG. 3A is a plan view of the first substrate 300 having a groove engraved on the surface, which groove constitutes the channels of the microchip. FIG. 3B is a plan view of the second substrate 310 having a hole engraved on the back side, which hole constitutes the section wherein the stirring bar of the microchip is placed. FIGS. 3C and D show a plan view and a front view of the microchip 3 of the third embodiment, wherein the substrate 300 and the substrate 310 are laminated with each other such that the opening sections of the groove and hole are facing inward.

In FIG. 3A, the first substrate 300 has a groove constituting the third channel 306 on the surface such that one end of the channel is connected to the merged channel 303 in the downstream of the narrowing section 305 but the upstream of the waste liquid reserving section 304.

In FIG. 3B, the second substrate 310 has a penetrating hole which constitutes the third inlet 318 at the position corresponding, when the second substrate 310 is laminated with the first substrate 300, to the other end of the third channel 306 on the first substrate 300. The stirring section 313 is provided similarly with that of the microchip 2 of the second embodiment.

The microchip 3 of the third embodiment of the present invention shown in FIGS. 3C and D is obtained by laminating the substrates such that they closely contact with each other as in the first embodiment.

The microchip of the third embodiment has a tube not shown connected to the third inlet 318, and a liquid sending pump or a syringe not shown is connected via the tube to introduce an anticoagulation agent for inhibition of coagulation of the mixture into the third channel 306. Since introduction of this anticoagulation agent prevents obstruction of channels in the microchip due to coagulation of the mixture used for monitoring, stable monitoring can be carried out. Examples of the anticoagulation agent will be described later, and include an EDTA solution.

Next, the blood monitoring device of the present invention using the microchip of the present invention will now be described.

Figure 4:
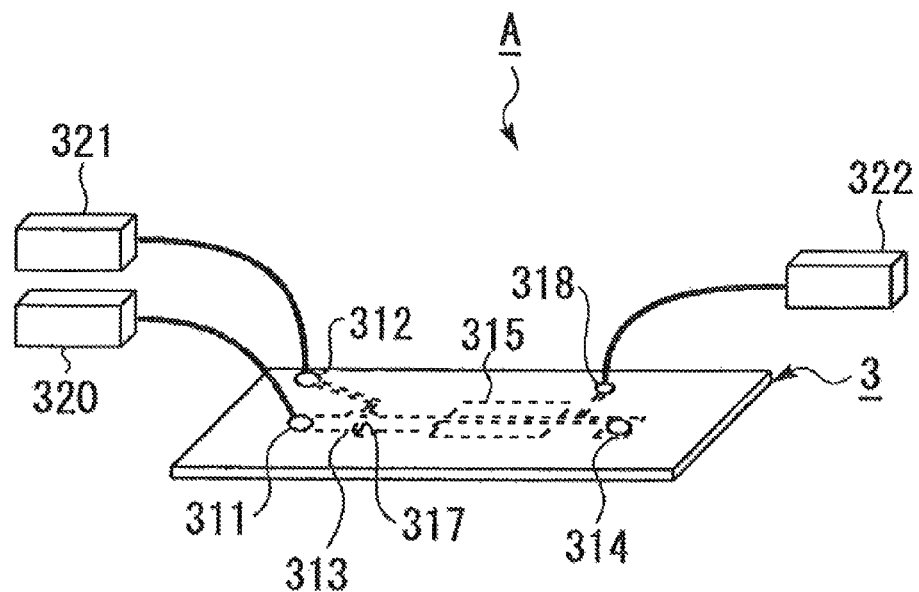
FIG. 4 is a conceptual diagram showing a blood monitoring device A of the first embodiment of the present invention.

FIG. 4 is a conceptual diagram showing a blood monitoring device A as the first embodiment of the blood monitoring device of the present invention, in which the microchip 3 of the third embodiment constituted by transparent substrates is incorporated. The first embodiment will now be described based on FIG. 4.

To the first inlet 311 of the microchip 3, the first liquid sending pump 320 for supplying anticoagulated blood is connected via a tube. To the first liquid sending pump 320, a pressure sensor not shown is connected.

To the second inlet 312, the second liquid sending pump 321 for supplying an anticoagulation-releasing agent is connected via a tube. The anticoagulation-releasing agent is an agent for releasing anticoagulation treatment of anticoagulated blood.

To the third inlet 318, the third liquid sending pump 322 for supplying a blood coagulation-preventing agent is connected via a tube.

Anticoagulated blood pumped from the liquid sending pump 320 joins the anticoagulation-releasing agent injected from the liquid sending pump 321 in the microchip 3 and the resultant is mixed by stirring with the stirring bar 317 in a stirring section 313, followed by flowing down the merged channel to reach an inducing material-placing section 315 coated with a thrombus formation-inducing material.

By observation of thrombus formation in the thrombus formation chamber which is the merged channel in the inducing material-placing section 315 visually or with a camera not shown, blood monitoring can be carried out. Alternatively, by measuring the pressure of the inside of the channel with a pressure sensor connected to the liquid sending pump 320, a more quantitative blood monitoring can be carried out.

The mixed solution containing blood, which passed through the thrombus formation chamber is mixed with the blood coagulation-preventing agent introduced from the third pump 322 connected to the third inlet 318 via a tube, and smoothly discharged from the outlet 314.

Figure 5:
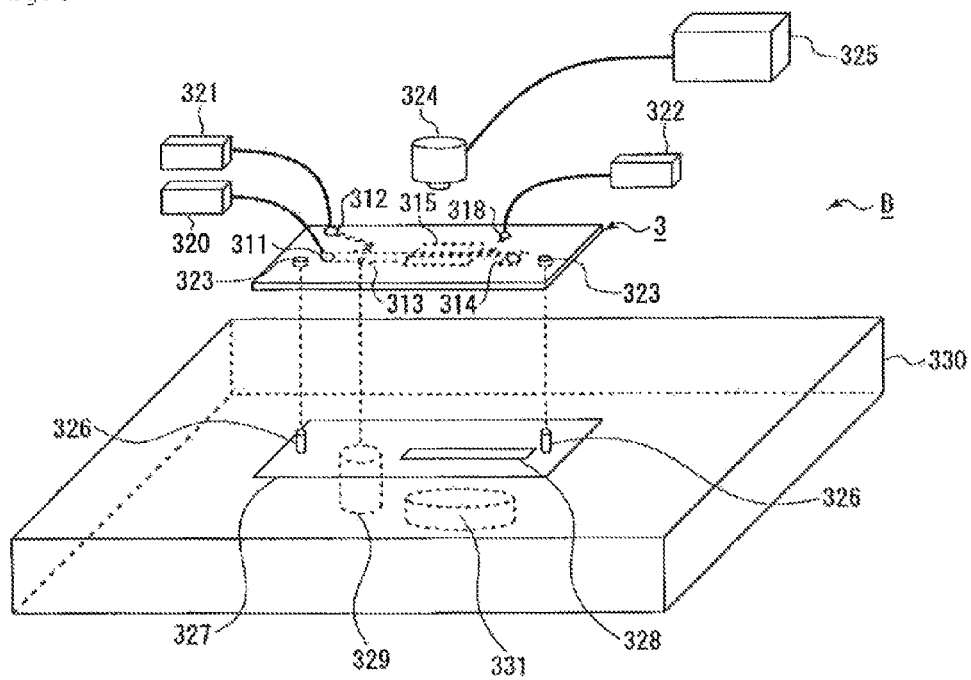
FIG. 5 is a conceptual diagram showing a blood monitoring device B of the second embodiment of the present invention.
Figure 6:
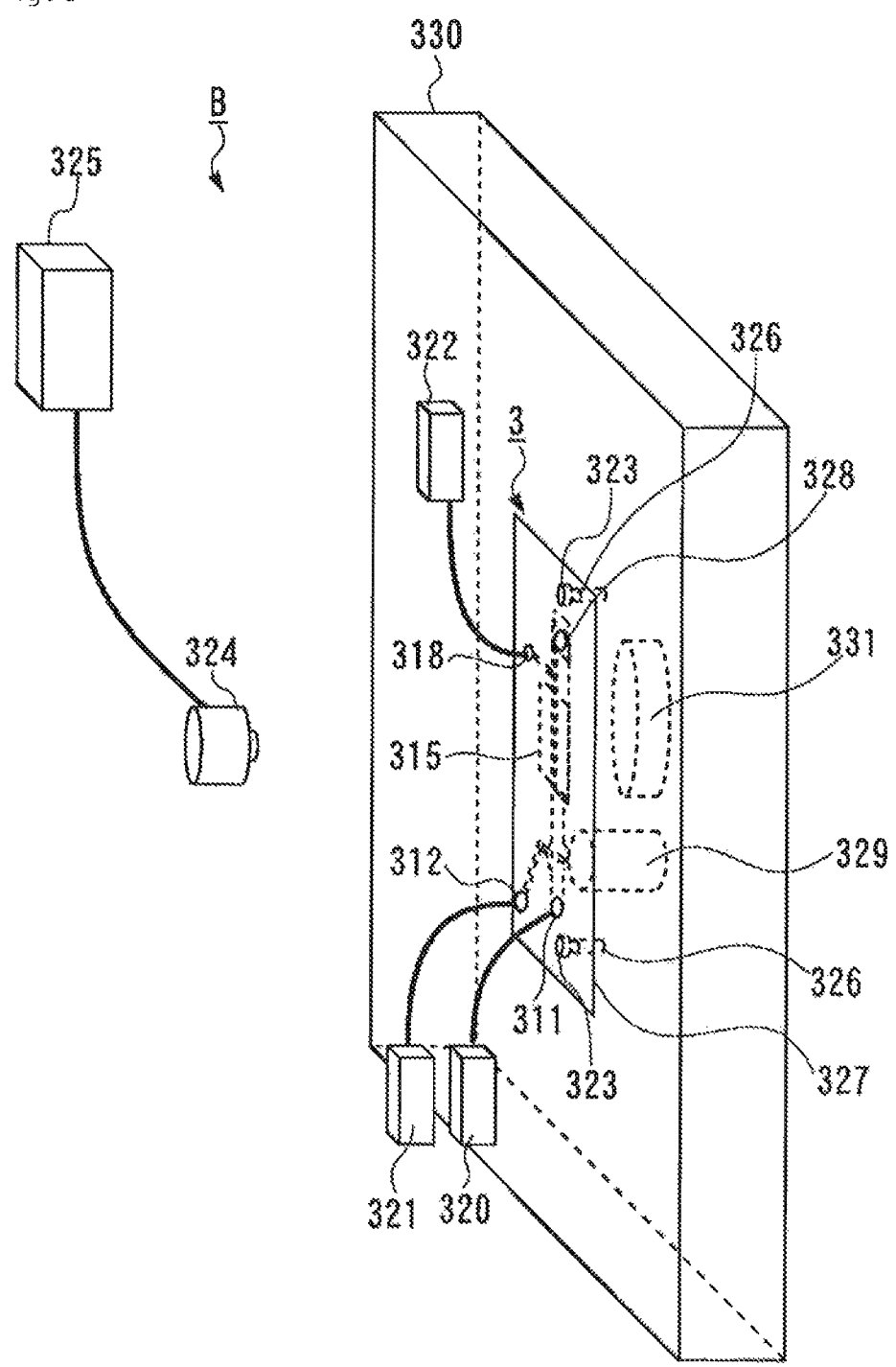
FIG. 6 is a conceptual diagram showing a state wherein the blood monitoring device B of the second embodiment of the present invention was vertically placed.

FIG. 5 and FIG. 6 are conceptual diagrams of a blood monitoring device B as the second embodiment of the blood monitoring device of the present invention, in which the microchip 3 of the third embodiment constituted by transparent substrates is incorporated. The second embodiment will now be described based on FIG. 5. The difference of the present embodiment from the first embodiment is that the device is systematized. Descriptions overlapping with those of the first embodiment will be omitted.

The microchip 3 used in the blood monitoring device B is constituted in the same manner as in the first embodiment except that the second liquid sending pump 321 which supplies a platelet-activating agent is connected via a tube to the second inlet 312. The platelet-activating agent is an agent for activating platelets. The blood monitoring device B is a system wherein, in addition to the blood monitoring device A, the CCD camera 324 for observation of the thrombus formation chamber, the image analyzer 325, the heater 327, the illumination 331 and a computer not shown are arranged, which system is capable of imaging the process of thrombus formation, and monitoring and controlling the pressure inside the microchip.

On the microchip 3, two fixation holes 323 are provided, and by fitting the holes to chip-fixing pins 326 provided on the stage 330 for placing the microchip 3, measurement can be carried out with the microchip fixed. At the position immediately under the microchip on the stage 330, a heater 327 is placed, and by warming the microchip to 37° C., the measurement can be carried out under a condition more close to in vivo.

An outline of the blood monitoring method of the present invention using this blood monitoring device B will now be described.

The anticoagulated blood having inflowed from the first pump 320 and the agent for activating platelets having inflowed from the second pump 321 are mixed together by a stirring bar rotated by the magnetic stirrer 329, and flows down while forming a thrombus in the thrombus formation chamber in the inducing material-placing section 315. At the position of the stage 330 corresponding to the thrombus formation chamber, the illumination slit 328 is provided, and the thrombus formation chamber is illuminated by the light source 331 to allow the camera 324 to take photographs which are then analyzed by the image analyzer 325.

In this blood monitoring device B, the state of thrombus formation can be grasped in more detail by image analysis. Especially in cases where platelets or leukocytes are fluorescently labeled with quinacrine or the like to monitor adhesion and aggregation thereof to collagen, it is possible, by monitoring brightness per unit area resulting from fluorescent coloring, to express the monitoring results in values and obtain the results as data. Since a thrombus formed in the blood flow is a white thrombus containing large amounts of platelets and leukocytes, and a thrombus obtained by activation of platelets in an anticoagulated state is also a white thrombus constituted by platelets, it is possible to easily analyze the process of thrombus formation by monitoring the process of change in the color of blood from red to white and the ratio between, and the areas of, the red and white using the present device. Further, by image analysis and by measurement of change in the pressure on the pump 320, comprehensive monitoring of the state of thrombus formation can be carried out.

In FIG. 6, the blood monitoring device B is vertically placed such that the first channel and the second channel of the microchip 3 are in the lower side and the merged channel is in the upper side, that is, such that the inlet 311 and the inlet 312 are in the lower side and the outlet 314 is in the upper side. If the microchip 3 is placed horizontally as shown in FIG. 5, the stirring section 313 protrudes upward. In this case, even after the inflow of blood into the stirring section 313, a certain amount of air may remain therein. If the microchip 3 is vertically placed like this, even if bubbles were formed during mixing in the stirring section, the bubbles are naturally expelled to the upper side, so that the mixing by stirring can be carried out stably and uniformly without being disturbed by the bubbles.

The microchip 4 of the fourth embodiment of the present invention and a thrombus monitoring device C using the microchip 4 will now be described.

Figure 10:
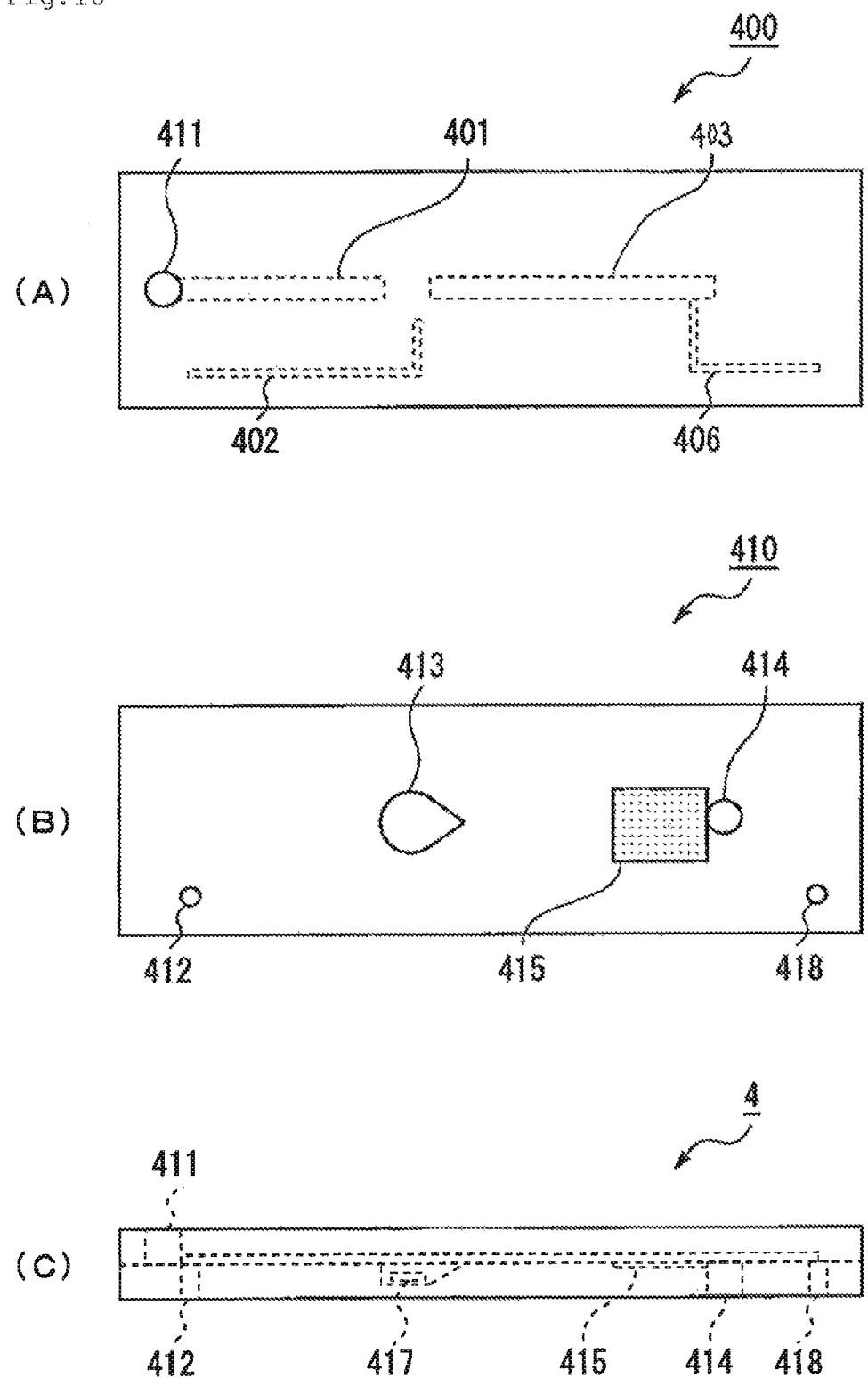
FIG. 10 is a conceptual diagram showing important parts of the microchip 4 of the fourth embodiment of the present invention. (A) shows the first substrate of the microchip 4; (B) shows the second substrate of the microchip 4; (C) shows a front view of a completed microchip 4.

FIG. 10 is a conceptual diagram showing the microchip 4 of the fourth embodiment of the present invention. FIG. 10A shows the first substrate 400, FIG. 10B shows the second substrate 410, and FIG. 10C is a diagram showing a completed microchip 4.

The microchip 4 is constituted by the substrate 400 and the substrate 410 bonded to each other. On the substrate 400, a penetrating hole corresponding to the first inlet 411 is provided, and grooves corresponding to the first channel 401, second channel 402, merged channel 403 and third channel 406 are further provided.

On the substrate 410, penetrating holes corresponding to the second inlet 412, third inlet 418 and outlet 414 are provided; a hole corresponding to the stirring section 413 are further provided; and a thrombus-inducing material is coated on the portion corresponding to the thrombus formation chamber 415.

FIG. 10(C) is a diagram showing the microchip 4 constituted by the substrate 400 and the substrate 410 bonded to each other. When it is placed such that the substrate 410 is on the lower side, the first inlet 411 opens upward, and the second inlet 412, third inlet 418 and outlet 414 open downward. The substrate 400 and the substrate 410 are bonded together such that the grooves corresponding to the first channel 401, second channel 402 and merged channel 403 on the substrate 400 and the groove corresponding to the stirring section 413 and the portion coated with the thrombus-inducing material on the substrate 410 are facing to each other, and that the stirring bar is placed in the stirring section. The second inlet 412 and the third inlet 418 on the substrate 410 are connected to the left end of the second channel 402 and the right end of the third channel 406, respectively, on the substrate 400. The outlet 414 on the substrate 410 is connected to the right end of the merged channel 403 on the substrate 400.

Figure 11:
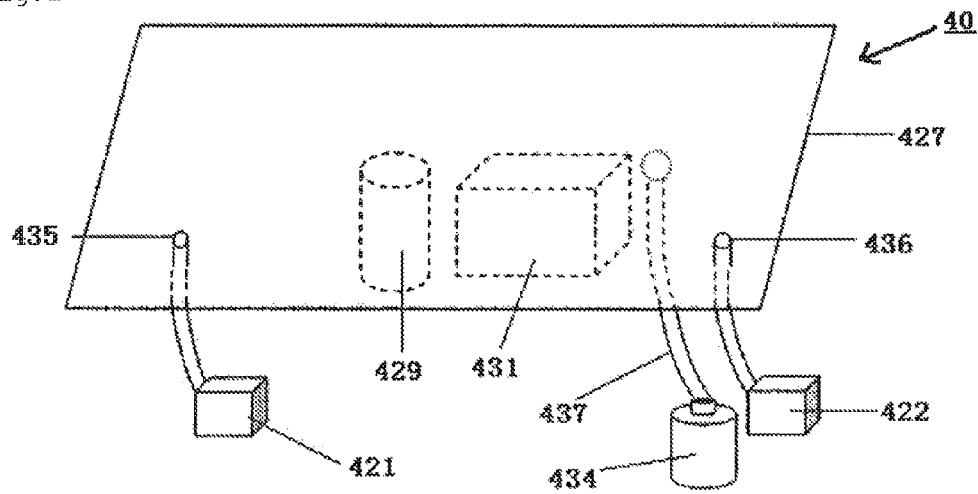
FIG. 11 is a conceptual diagram showing the stage of the thrombus monitoring device C of the present invention.

FIG. 11 shows the stage 40 on which the microchip 4 is placed.

On the stage 40, the first connection nozzle 435 and the second connection nozzle 436 to be connected to the second inlet 412 and the third inlet 418, respectively, on the microchip 4 are provided. These nozzles are made of a stainless steel or rigid plastic and connected to the respective inlets of the microchip 4 from beneath. By being connected in such a manner, these nozzles have a function to accurately guide the microchip 4 to a predetermined position on the stage 40 for optimizing its position relative to monitoring instruments such as a camera and to a magnetic stirrer to drive a stirring bar. The first and second connection nozzles are connected to a second pump 421 and third pump 422, respectively, via tubes.

From the first connection nozzle 435, an agent for releasing anticoagulation treatment (e.g., calcium chloride), a platelet-activating reagent (e.g., ADP), a fibrinolytic agent (e.g., tPA) or the like is allowed to flow into the second channel 402 through the second inlet 412. To prevent obstruction of the portion of the merged channel 403 downstream of the thrombus-inducing material—applied region 415, and the discharging tube 437, a blood coagulation-preventing agent is allowed to flow from the second connection nozzle 436 to the third channel 406 through the third inlet 418.

The amount of the agent for releasing anticoagulation treatment allowed to inflow from the second inlet 412 is smaller and the flow rate of the agent is required to be controlled more precisely, in comparison with the blood coagulation-preventing agent allowed to inflow from the third inlet 418. Therefore, the diameter of the first connection nozzle 435 is preferably designed to be smaller than that of the second connection nozzle 436. If the diameter of the first connection nozzle 435 is designed to be smaller, even in cases where a small amount of a liquid is allowed to inflow, precise and stable liquid transfer is possible due to a small dead volume of the nozzle tip.

The outer diameters of the first connection nozzle and the second connection nozzle are designed such that these can be connected to the holes of the second inlet 412 and the third inlet 418, respectively, without causing leakage. For example, the first connection nozzle having an outer diameter of about 0.5 to 1.5 mm, the second connection nozzle having an outer diameter of about 1 to 3 mm, the second inlet whose hole has a diameter of about 0.5 to 1.5 mm, and the third inlet whose hole has a diameter of about 1 to 3 mm are preferred.

The first and second connection nozzles 435 and 436 have functions as positioning guides for a magnetic stirrer 429 which drives the stirring bar stored in the stirring section 413, and the magnetic stirrer 429 is placed beneath the stirring section 413 of the microchip 4 positionally-fixed by being connected to the first connection nozzle 435 and the second connection nozzle 436. Under the merged channel 403, the transparent heater 427 which controls the temperature of the microchip 4 is placed, and a thrombus on the thrombus-inducing material-placing section 415 of the merged channel 403 is illuminated by the illumination 431 under the merged channel 403. On the stage 40, a hole for discharging waste liquid opens at the position corresponding to the position of the outlet 414 of the microchip 4 and is connected to the waste liquid tank 434 via the waste liquid tube 437. A negative pressure is maintained in the waste liquid tank 434 and waste liquid is aspirated from the outlet 414.

Figure 12:
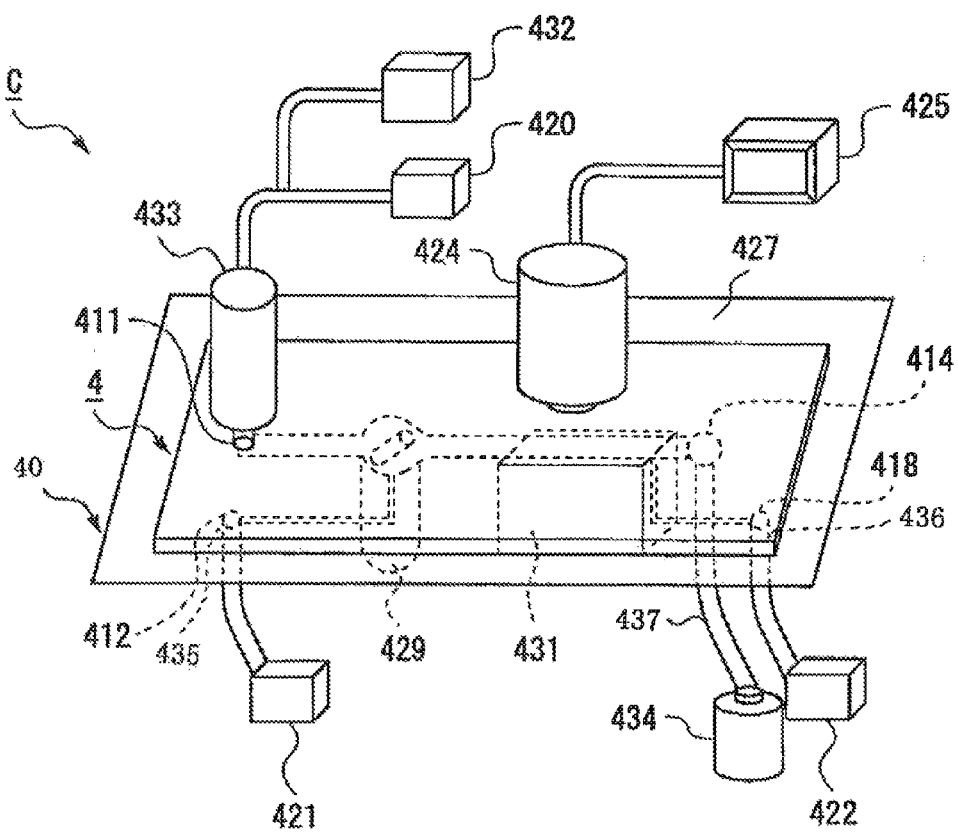
FIG. 12 is a conceptual diagram showing the thrombus monitoring device C of the present invention.

FIG. 12 is a conceptual diagram showing the thrombus monitoring device C of the present invention. The thrombus monitoring device C is constituted by placing: the microchip 4 on the stage 40; and, on the top, the blood reservoir 433 connected with the first pump 420 and the pressure sensor 432, and the CCD camera 424 connected with the image analyzer 425.

Through the first inlet 411, anticoagulated blood is allowed to flow. The anticoagulated blood is stored in the blood reservoir 433, and the blood reservoir 433 is connected to the first pump 420. From the first pump 420, mineral oil is injected to the blood reservoir 433, and the blood is pushed by the injected mineral oil out into the microchip 4. The inflow pressure of the blood is measured by the pressure sensor 432.

Above the region 415 to which a thrombus-inducing agent was applied, the CCD camera 424 is placed. The CCD camera 424 is made to be capable of moving along the merged channel and takes still images of the merged channel 403 regularly according to a program. The CCD camera 424 can capture still images while moving constant distances, to capture the entire merged channel 403 as a sequence of still images.

Also in cases where the microchip 1 of the first embodiment is used, if it is placed horizontally, the stirring section protrudes upward, so that the microchip is preferably placed vertically as in the blood monitoring device B. On the other hand, in cases where the microchip 2 of the second embodiment is used, even if it is placed horizontally, the stirring section protrudes downward, so that the microchip can be placed either horizontally or vertically.

The reason why the microchip 1 and the microchip 3 are not constituted in the same manner as the microchip 2 is that, conventionally, in cases where a microchip was subjected to injection molding, only grooves were molded and an inlet and an outlet were provided later as required, so that there are no dies by which the grooves and the holes can be molded at the same time. On the first substrate 200 of the microchip of the second embodiment, grooves and holes coexist, but these holes are ones formed later. Therefore, by preparing a die capable of molding grooves and holes at the same time, the stirring section of the microchip 1 and the microchip 3 can be made to protrude downward.

Further, the blood monitoring method of the present invention using the blood monitoring device B will now be described in detail.

First, based on FIG. 5, and referring to FIG. 3 for details of the microchip 3, the first embodiment of the blood monitoring method of the present invention using the microchip 3 of the present invention will be described.

To the first inlet 311, an inverted syringe not shown containing anticoagulated blood, which syringe is provided between the first liquid sending pump 320 and a tube, is connected. The device is constituted such that, in the first liquid sending pump 320, a liquid which does not mix with blood and has a specific gravity smaller than blood is filled, and the liquid is injected to the syringe containing the blood and overlaid on the blood, thereby ejecting the blood into the microchip 3 through the liquid having a specific gravity smaller than blood.

Examples of the liquid having a specific gravity smaller than blood include various oils such as liquid paraffin, mineral oil and silicone oil; and physiological saline. Like this, by indirectly ejecting blood, it is possible to prevent contamination of the liquid sending pump and the pressure sensor with the blood.

The pump used may be a common commercially available pump, and may also be a syringe pump driven by a constant air pressure or by inverting the syringe such that the plunger is in the upside and putting a weight on the plunger.

Examples of the anticoagulation agent used for the anticoagulation treatment by which coagulation of blood is inhibited include sodium or potassium citrate, sodium or potassium oxalate, ACD (Acid Citrate Dextrose), and an ethylenediaminetetraacetic acid (EDTA) salt. Such an anticoagulation agent can be used as a powder, a freeze-dried product or a solution such as an aqueous solution. Among these anticoagulation agents, 3.2% sodium citrate which is commonly used is preferred since it can be easily obtained. In this case, 1 volume of this anticoagulation agent is preferably added to 9 volumes of blood.

Examples of other anticoagulation agents available include heparin, hirudin, hirulog (C-terminal region peptide of hirudin), aprotinin, anti-thrombin antibodies, thrombin aptamers and corn-derived trypsin inhibitors (1977. J. Biol. Chem 252. 8105). The anticoagulation agents may also be used in combination.

Examples of the method for collection of blood as a sample for measurement, by which anticoagulated blood can be obtained include: blood collection carried out with a syringe or a vacuum blood collection tube wherein the above-described anticoagulation agent was placed in advance; and addition of the anticoagulation agent to blood immediately after blood collection.

It is also possible to add heparinase and an anticoagulation agent suitable for the purpose of monitoring after collection of blood using a vacuum blood collection tube or the like containing heparin, and allow degradation of heparin by heparinase, thereby replacing heparin with the anticoagulation agent suitable for the purpose of monitoring. Further, similarly, it is possible to collect anticoagulated blood suitable for the purpose of monitoring by collecting blood with a vacuum blood collection tube containing citric acid and then adding thereto calcium chloride and a coagulation factor inhibitor suitable for the purpose of monitoring, such as corn-derived trypsin inhibitor or a thrombin aptamer.

To the second inlet 312, the second pump 321, to which pump an agent tube not shown filled with an anticoagulation-releasing agent is connected, is connected.

Examples of the anticoagulation-releasing agent include, in cases where anticoagulation treatment by a chelating agent such as citric acid is to be released, calcium compounds which are donors of free calcium, including: calcium halides such as calcium chloride, calcium bromide and calcium iodide; calcium salts of inorganic acids, such as calcium phosphate, calcium sulfate, calcium nitrate and calcium bicarbonate; and calcium salts of organic acids such as formic acid, acetic acid, propionic acid, butyric acid, alginic acid, lactic acid, gluconic acid, glyceric acid and glycerophosphoric acid.

In cases where anticoagulation treatment by a coagulation factor inhibitor (anticoagulation agent) is to be released, the anticoagulation-releasing agent can be appropriately selected and used depending on the coagulation factor inhibitor. Examples of the anticoagulation-releasing agent available in the case of anticoagulation treatment using heparin include protamine, heparinase and anti-heparin antibodies; and examples of the anticoagulation-releasing agent available in the cases of anticoagulation treatment using hirudin, hirulog and aprotinin include anti-hirudin antibodies, anti-hirulog antibodies and anti-aprotinin antibodies, respectively.

Further, in cases where anticoagulation treatment by an anti-thrombin antibody, a coagulation factor inhibitor, is released, completely-inactivated thrombin such as PPACK thrombin, degradation products of thrombin, synthetic peptides having an antibody recognition epitope in thrombin, and the like can be used as an anticoagulation-releasing agent.

To minimize the influence of the antibody used for the anticoagulation treatment or release of anticoagulation on the complement system, it is preferred to use an antibody from which the Fc domain was removed by papain or the like or an antibody such as a chicken egg antibody which does not have a human complement system-activation capacity.

In cases where a thrombin aptamer which is a single-stranded oligo DNA (Blood. 1993 Jun. 15; 81 (12): 3271-6. and J Mol Biol. 1997 Oct. 10; 272 (5): 688-98) is used as the anticoagulation agent, a substance which binds to the thrombin aptamer and inhibits its function, such as antisense DNAs and antisense RNAs against the thrombin aptamer can be used as an anticoagulation-releasing agent. By using two types of thrombin aptamers recognizing the exosites I and II in combination, a drastically higher anticoagulation effect can be obtained compared to cases where they are used solely. The antisense DNA used in this case may be one against a part of the thrombin aptamer as long as it makes the anti-thrombin function of the thrombin aptamer substantially ineffective.

The anticoagulated blood which was introduced from the first inlet 311 and passed through the first channel 301 and the anticoagulation-releasing agent which was introduced from the second inlet 312 and passed through the second channel 302 join together and reach the stirring section 313, followed by being mixed uniformly by the stirring bar 317. The resulting mixture containing the blood flows, while the anticoagulation treatment being released, through the narrowing section 305 of the merged channel 303 and the inducing material-placing section 315, thereby inducing thrombus formation. The blood which passed through the thrombus formation chamber is discharged from a discharge pipe not shown connected to the outlet 314.

The blood coagulation capacity of the blood can be evaluated at this time by visual monitoring of the flow rate of the blood or measurement of the pressure by the pressure sensor connected to the first pump 320. Further, by monitoring the thrombus formation chamber visually or with the camera 324, the state of the blood coagulation can be investigated.

In the syringe connected to the first inlet 311, an anticoagulated, for example, sodium citrate-treated whole blood and platelet-rich plasma (first liquid) are filled. In the agent tube connected to the second inlet 312, an anticoagulation-releasing agent, for example, a calcium chloride solution (second liquid) is filled. The concentration of the second liquid is adjusted to about 5 to 20 millimolar at which the coagulation cascade of the first liquid is initiated. The mixture of the first liquid and the second liquid is stirred by the stirring bar 317 and inflows into the thrombus formation chamber in the inducing material-placing section 315. Thrombus formation can be easily monitored using such a device wherein blood passing through the inducing material-placing section 315 which is transparent is monitored.

Monitoring of the thrombus formation can be visually evaluated by allowing the blood to flow for a certain period of time followed by removal of the blood from the inside of the thrombus formation chamber. In cases where the pumps for transferring the first liquid and the second liquid are air-driven, by transferring the first liquid and the second liquid at constant pressures, thrombus formation on collagen can be monitored based on decrease in the blood flow discharged from the discharge pipe. In cases where platelet-rich plasma is used, observation can be easily carried out since the thrombus is highly visible, and it is also possible to observe thrombus formation with the naked eye. It is also possible to label platelets fluorescently with mepacrine or the like and monitor them under a fluorescence microscope.

The second embodiment of the blood monitoring method of the present invention will now be described in the same manner as in the first embodiment, referring to FIG. 5 and FIG. 3.

The difference of the present embodiment from the first embodiment is that, as the blood, anticoagulated whole blood or platelet-rich plasma is used, and as the agent which is allowed to react with the blood, an agent for activating platelets is used. Descriptions overlapping with the first embodiment will be omitted.

The present embodiment will now be described based on FIG. 6.

The blood in the syringe connected to the first inlet 311 of the microchip 3 is anticoagulated. The anticoagulation treatment can be carried out as described above, and among these, citric acid treatment is preferred.

In the agent tube connected to the second inlet 312, an agent for activating platelets is filled. Examples of the agent for activating platelets include ADP, collagen, thrombin and ristocetin.

The anticoagulated blood which was introduced from the first inlet 311 and passed through the first channel 301 and the agent for activating platelets which was introduced from the second inlet 312 and passed through the second channel 302 join together and reach the stirring section 313, followed by being mixed uniformly by the stirring bar 317. The resulting mixture containing the blood flows, while platelets being activated, through the narrowing section 305 of the merged channel 303 and the inducing material-placing section 315, thereby causing adhesion and aggregation of the platelets to allow platelet thrombus formation.

Platelet function can be evaluated at this time by measurement of the blood flow rate and the pressure. Further, by monitoring the thrombus formation chamber visually or with the camera 324, the state of thrombus formation by platelets can be investigated. By this, it is possible to monitor platelet function such as adhesion and aggregation specifically in an environment similar to that in the human body.

The third embodiment of the blood monitoring method of the present invention will now be described in the same manner as in the first embodiment, referring to FIG. 5 and FIG. 3.

The difference of the present embodiment from the first embodiment is that, as the blood, whole blood or platelet-rich plasma is used, and this is allowed to flow as it is in the first channel 301 and to form a thrombus in the thrombus formation chamber, and after formation of the thrombus to a certain extent, a solution of a thrombolytic agent as an agent which can react with the blood is allowed to flow in the second channel 302. Descriptions overlapping with the first embodiment will be omitted.

The present embodiment will now be described based on FIG. 5.

The blood in the syringe connected to the first inlet 311 of the microchip 3 is not anticoagulated in especial.

In the agent tube connected to the second inlet 312, a thrombolytic agent is filled. Examples of the thrombolytic agent include urokinase, plasmin and tPA.

The anticoagulated blood which was introduced from the first inlet 311 and passed through the first channel 301 passes through the stirring section 317 and forms a thrombus in the thrombus formation chamber. At this time, even if the stirring bar 317 was subjected to coagulation inhibition treatment, blood coagulation occurs in some cases in the stirring section 313. To prevent this, it is preferred that the stirring bar 317 be made to be static without being rotated, and it is more preferred that the stirring section 313 be also subjected to coagulation inhibition treatment with PVLA or the like.

When formation of a thrombus to a certain extent was observed, the thrombolytic agent is introduced from the second channel 302, and the thrombolytic agent which passed through the second channel 302 reaches the stirring section 313, followed by being mixed uniformly by the stirring bar 317. The resulting mixture containing the blood reaches the thrombus formation chamber and lyses the formed thrombus.

By monitoring the flow rate and the pressure of the blood at this time, the thrombolysis can be evaluated. Further, by monitoring the thrombus formation chamber visually or with the camera 324, the state of the thrombolysis can be investigated.

The thrombus monitoring method of the present invention will now be described using FIGS. 10 to 12.

The microchip 4 is placed on the stage 40. The first connection nozzle 435 and the second connection nozzle 436 are inserted to the second inlet 412 and the third inlet 418, respectively, and the stirring section 413 is placed on the magnetic stirrer 429 of the stage 40; and the CCD camera 424 is placed above, and the illumination 431 is placed beneath, the thrombus-inducing agent-placing section 415 in the merged channel 403. On the stage 40, the heater 427 is placed, which keeps the temperature of the microchip 4 constant. The temperature of the microchip 4 is preferably maintained at about 37° C.

The reagent, blood and thrombus-inducing material to be used are determined appropriately depending on the purpose of measurement.

For example, in cases where the thrombus formation capacity comprehensively reflecting blood coagulation, platelet function, fibrinolysis and the like is measured, the following method for measurement is preferred.

The blood reservoir 433 contains anticoagulated whole blood. The anticoagulation treatment is not restricted, and it is preferably carried out with citric acid or citric acid and a corn-derived trypsin inhibitor. The blood reservoir 433 is connected to the first pump 420 and the first inlet 411. Mineral oil is injected to the blood reservoir 433 from the first pump 420, and the blood is injected to the microchip 4 from the first inlet 411. Through the first connection nozzle 435, calcium chloride is injected from the second inlet 412. The blood and calcium chloride are allowed to flow through the first channel and the second channel, respectively, and join together in the stirring section 413, followed by being mixed by the stirring bar.

The volume ratio between the blood and the calcium chloride to be mixed is preferably 10:2 to 100:1. In cases where the ratio is larger than 10:2, thrombus formation suitable for monitoring does not occur since the blood is diluted by the calcium chloride, and in cases where the ratio is smaller than 100:1, the amount of the calcium chloride solution is very small, so that the flow rate may be too small for accurate liquid transfer by the second pump 421. The concentration of the calcium chloride solution is adjusted such that it can make the anticoagulation treatment with citric acid ineffective (released). The first and second pumps are controlled such that the liquid 413 stays in the mixing section for 5 seconds to 3 minutes to be stirred. In cases where the liquid is stirred for only 5 seconds or less, the stirring may be insufficient, and in cases where the liquid is stirred for more than 3 minutes, blood coagulation may proceed in the stirring section 413.

The mixture containing blood passes through the merged channel 403 and then the thrombus formation chamber 415. The thrombus-inducing material allowed to adhere to the thrombus formation chamber 415 is preferably a coating containing a mixture of collagen and tissue thromboplastin.

By inclusion of collagen and tissue factor, phenomena involved in thrombus formation such as adhesion and aggregation on collagen and activation of the coagulation system by the tissue factor are comprehensively induced. The blood which passed through the thrombus formation chamber 415 constituted by the merged channel 403 and the thrombus-inducing material-placing section 415 is mixed with the blood coagulation-preventing agent injected from the second nozzle 436 via the third channel, and discharged from the outlet 414, followed by passing through the discharging tube 437 and being stored in the waste liquid tank 434.

The blood coagulation-preventing agent is used for prevention of obstruction and increase in the pressure due to blood coagulation in the waste liquid moving from the outlet 414 to the waste liquid tank 434 can be used, and examples thereof include chelating agents such as EDTA and citric acid; acidic and alkaline solutions; alcohols; and denaturants such as guanidine, urea and SDS.

Progression of thrombus formation in the merged channel causes increase in the pressure on the portion where mineral oil is transferred to the blood reservoir 433. By observation of increase in the pressure by the pressure sensor 432, it is possible to judge the state of obstruction inside the channel.

The process of thrombus formation in the microchip 4 is illuminated from the lower part by the illumination 431 using a white LED, and pictures thereof are taken by the camera 424. The camera 424 takes pictures sequentially at the same positions while moving constant distances at designated constant time intervals, thereby enabling grasping of the thrombus formation in the entire merged channel 403 with time.

EXAMPLES

The present invention will now be described in more detail by way of specific examples, but the present invention is not restricted thereto.

Example 1

[Preparation of Microchip and Blood Monitoring Device]

Two transparent substrates, that is, the first substrate 100 shown in FIG. 1A and the second substrate 110 shown in FIG. 1B (injection-molded products manufactured by Richell Corporation) were prepared. The first substrate 100 and the second substrate 110 were laminated with each other using an adhesive such that the side of the first substrate 100 where the channels open and the side of the second substrate 110 where the hole constituting the stirring section 113 opens face to each other, to provide the microchip 1 shown in FIG. 1C and FIG. 1D. The depth of each channel was 0.12 mm, the width of the first channel 101 was 1.2 mm, and the width of the narrowing section of the merged channel 103 was 0.3 mm. As the stirring bar 117, an iron cylinder coated with PVLA, having a diameter of 1 mm and a length of 2 mm was placed in the stirring section 113. The hole constituting the stirring section 113 was a penetrating hole whose cross section was circular, having an inner diameter of 3 mm and a depth of 1.2 mm. Collagen was applied to the inducing material-placing section 115 of the second substrate 110. The stirring bar 117 was rotated at 100 to 200 rpm by magnetic force of a stirrer.

Pumps were connected to the first inlet and the second inlet of the prepared microchip 1 to prepare a blood monitoring device.

[Confirmation of Mixing State and Remaining Air]

Purified water as the first liquid was injected from the first inlet 111 of the microchip 1 at a speed of 20 μL/min and red ink as the second liquid was injected from the second inlet 112 of the microchip 1 at a speed of 10 μL/min, followed by being stirred in the stirring section 113 and discharged from the outlet 114. At this time, the two liquids were found to be uniformly mixed with each other.

In cases where the microchip 1 was horizontally placed such that the first substrate 100 was in the lower side and the second substrate 110 was in the upper side to prepare a blood monitoring device, the first liquid and the second liquid were smoothly mixed together, but in some cases, a certain amount of air remained in the stirring section 113.

On the other hand, in cases where the microchip 1 was vertically placed such that the first inlet 111 of the microchip 1 was in the lower side and the outlet 114 thereof was in the upper side, no air remained.

Example 2

[Preparation of Microchip]

Two transparent substrates, that is, the first substrate 200 shown in FIG. 2A and the second substrate 210 shown in FIG. 2B (injection-molded products manufactured by Fluidware) and the third substrate 220 shown in FIG. 2C which is a transparent acrylic plate were prepared. The first substrate 200 and the second substrate 210 were laminated with each other using an adhesive such that the side of the first substrate 200 where the channels open and the side of the second substrate 210 where the hole constituting the stirring section 213 opens face to each other. The opening of the hole of the stirring section 213 of the second substrate 200 was closed by the third substrate 220 using an adhesive, to provide the microchip 2 shown in FIG. 2D and FIG. 2E. The thickness of the second substrate 210 was 1.2 mm, which thickness corresponded to the depth of the hole constituting the stirring section 213. The shape of the hole constituting the stirring section 213 of the second substrate 210 was as shown in FIG. 2B and FIG. 2E, which hole had, in addition to a circular penetrating hole having an inner diameter of 3 mm, a triangular pyramid-shaped outflow passage having a three-dimensional slope. The depth of each channel was 0.25 mm, the width of the first channel 201 was 0.5 mm, the width of the narrowing section of the merged channel 203 was 0.2 mm, and the width of the second channel 202 was 0.15 mm, and application of collagen and placement of a stirring bar were carried out in the same manners as in Example 1.

[Preparation of Blood Monitoring Device and Confirmation of Mixing State]

The microchip 2 was horizontally placed such that the first substrate 200 was in the upper side and the third substrate 220 was in the lower side, and pumps were connected to the first inlet and the second inlet to prepare a blood monitoring device.

Purified water as the first liquid was injected from the first inlet 211 of the microchip 2 at a speed of 20 μL/min and red ink as the second liquid was injected from the second inlet 212 of the microchip 2 at a speed of 10 μL/min, followed by allowing the liquids to pass through the stirring section and discharging thereof from the outlet 214. At this time, the two liquids were found to be uniformly mixed with each other. No air remained in the stirring section 213.

Example 3

The microchip 2 and a blood monitoring device were prepared in the same manner as in Example 2 except that the stirring section 213 of the second substrate 210 in Example 2 was simply a circular penetrating hole having an inner diameter of 3 mm. Experiments to confirm the state of mixing were carried out in the same manner as in Example 2. As a result, the two liquids were uniformly mixed with each other, but in some cases, air remained in the stirring section.

Example 4

[Preparation of Microchip and Blood Monitoring Device]

In the same manner as in Example 1, the microchip 3 shown in FIG. 3 was prepared. However, in this case, the width of the third channel 306 was 0.2 mm, and 10 μL of a mixture of collagen type I (Nitta Gelatin Inc.) and PT reagent (Sysmex Corporation) was applied to the inducing material-placing section 315 of the second substrate 310. As the collagen type I, one having a concentration of 3 mg/ml was used. As the PT reagent, one prepared by dissolving 1 vial of PT reagent manufactured by Sysmex Corporation in 2 ml of purified water and dialyzing the resulting solution against purified water overnight, followed by mixing the resultant at a ratio of 1:1 was used. The shape of the stirring section 313 was the same with that in Example 2.

The microchip 2 was horizontally placed such that the second substrate 310 was in the upper side and the first substrate 300 was in the lower side, and the first to third pumps 320 to 322 were connected to the first to third inlets, respectively, to prepare the blood monitoring device B shown in FIG. 5.

[Blood Monitoring 1]

While controlling each pump such that a predetermined flow rate is achieved by execution of the steps of the program shown in Table 1 in the order mentioned from the upper side, whole blood, to which 1/10 volume of 3.2% sodium citrate was added and further to which a corn-derived trypsin inhibitor was added to a final concentration of 25 μg/ml, was allowed to inflow from the first inlet 311 of the microchip 3; 0.2 M $CaCl_2$ was allowed to inflow from the second inlet 312; and 0.5 M EDTA pH 10 was allowed to inflow from the third inlet 318. The blood after monitoring was discharged from the outlet 314.

The microchip 3 was placed vertically for the first 32 seconds (steps 1 and 2), during which $CaCl_2$ and whole blood were allowed to flow therein. After confirming that air was completely removed from the stirring section 313, the microchip was horizontally placed on the stage 330 such that the second substrate 310 is in the upper side and the first substrate 300 is in the lower side.

In a container (reservoir tank) having on its tip a tapered injection tube which can be directly inserted to the first inlet 311, 600 μL of the blood was placed, and mineral oil was further placed in the reservoir tank. The tip of the reservoir tank was directly inserted to the first inlet 311, and the reservoir tank was placed upside down, followed by connecting the first pump 320 to its back end via a tube. By operation of the first pump 320 according to the program, the blood was injected into the microchip 3 via mineral oil. Changes in pressure were measured by the pressure sensor of the first pump 320. The results are shown in FIG. 7A.

TABLE 1

| Operation time of each executed step (seconds) | Pump 1 (320) flow rate (μL/min.) | Pump 2 (321) flow rate (μL/min.) | Pump 2 (322) flow rate (μL/min.) |
| --- | --- | --- | --- |
| 12 | 0 | 30 | 0 |
| 20 | 200 | 20 | 80 |
| 10 | 20 | 4 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |
| 10 | 12 | 1 | 80 |
| 120 | 12 | 1 | 40 |

Example 5

[Blood Monitoring 2]

As in Example 4, the following monitoring was carried out using the blood monitoring device B shown in FIG. 5 using the microchip 3 shown in FIG. 3. Descriptions overlapping with those in Example 4 will be omitted, and only the difference therefrom will be described.

Whole blood to which 1/10 volume of 3.2% sodium citrate was added was allowed to inflow from the first inlet 311 (first pump 320), and 0.1 μM ADP solution was allowed to inflow from the second inlet 312 (second pump 321).

The third inlet 318 of the microchip 3 was closed and not used.

While controlling each pump according to the program shown in Table 2, whole blood was injected from the first inlet 311, and the 0.1 μM ADP solution was injected from the second inlet 312, into the microchip 3. The first steps 1 and 2 were for operating the pumps to remove air from the stirring section 313. Changes in pressure were measured by the pressure sensor of the first pump 320. The results are shown in FIG. 7B.

TABLE 2

| Operation time of each executed step (seconds) | Pump 1 (320) flow rate (μL/min.) | Pump 2 (321) flow rate (μL/min.) |
| --- | --- | --- |
| 10 | 0 | 30 |
| 30 | 60 | 10 |
| 10 | 20 | 4 |
| 3000 | 12 | 1 |

Example 6

Image Analysis of Thrombus Formation

Actually, the process of thrombus formation in Example 5 was observed as shown in the photographs in FIGS. 8A to D. The inside of the channel immediately after the inflow of the blood was red due to the blood, but white regions increased as white thrombi were formed in the channel.

The image analysis was carried out by the following method wherein pixel components of the blood monitoring device B were analyzed. Pixels having the B component (Blue) of a color image (RGB) smaller than the threshold (80) were counted to obtain the result of the image processing.

This corresponds to extraction of areas wherein R (Red) is enhanced. The threshold can be between 0 and 255, and was determined to be 80 by trial and error such that red areas were appropriately extracted.

Figure 9:
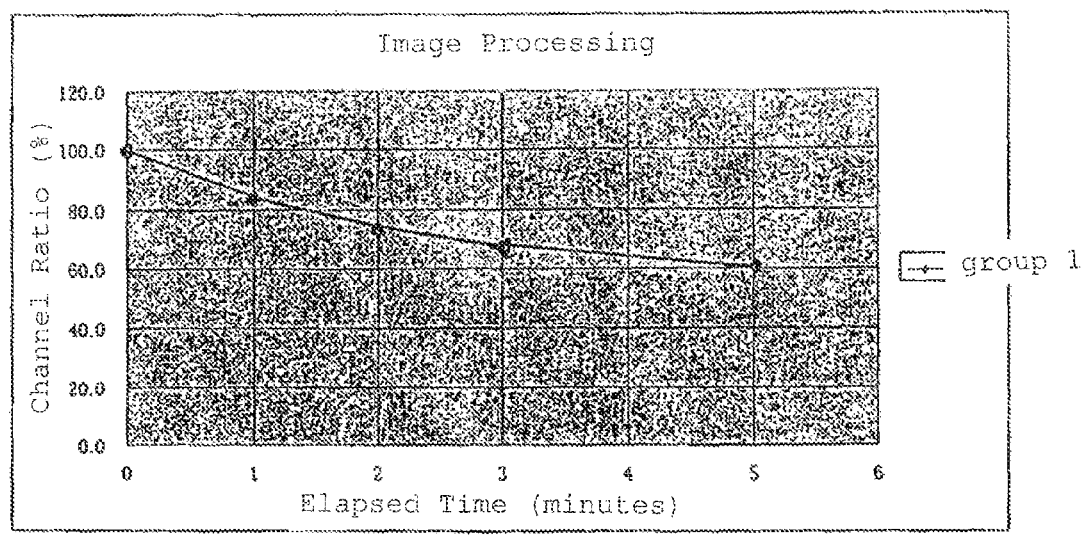
FIG. 9 shows a graph showing the results of FIG. 8 expressed in values.

Further, the ratio (channel ratio) against the pixel count corresponding to the channel area (about 86,000 dots) was calculated and pixels whose B component of RGB is smaller than the threshold (80) were counted. The results of the image processing were shown in a graph as the series 1. The result is shown in FIG. 9.

Example 7

An example of measurement of formation of a thrombus by coagulation and platelets using the thrombus monitoring device C shown in FIG. 12 will now be shown.

In FIG. 10A, all channels of the substrate 400 were grooves having a depth of 120 μm; the widths of the first channel 401 and the merged channel 403 were 250 μm; the width of the second channel 405 was 50 μm; and the width of the third channel 406 was 50 μm. In terms of the shapes and sizes of the inlets and outlets, the first inlet 411, the second inlet 412 and the third inlet 418 were in the shapes of circles having diameters of 2 mm, 0.7 mm and 2 mm, respectively. In terms of the thicknesses of the connection nozzles, the first connection nozzle 435 and the second connection nozzle 436 had outer diameters of 0.7 mm and 2 mm, respectively. The outlet 414 was in the shape of a circle having a diameter of 2 mm. As shown in FIG. 10B, the stirring section 413 was in the shape of a circle having a diameter of 1.5 mm and narrowing in fan-like fashion in the direction toward the downstream, and its depth was 1.2 mm. The stirring bar 417 was a magnetic stirring bar in the shape of a cylinder having a length of 2 mm and a diameter of 1 mm, whose surface was coated with nickel.

As the thrombus-inducing agent, 24 μL of a mixture of collagen type I (Nitta Gelatin Inc.) and PT reagent (Sysmex Corporation) was applied in a square shape sizing 1 cm×1 cm to the area corresponding to the thrombus-inducing material-placing section 415 of the substrate 410, and dried under reduced pressure at −0.08 MPa for 3 hours. The coating with the thrombus-inducing material was carried out such that the merged channel 403 was not passing the center of the square area on which the thrombus-inducing material was applied, that is, such that the merged channel 403 was passing 2.5 mm away from an edge of the square, when the substrate 400 and the substrate 410 were bonded to each other. The reason why the merged channel 403 was made not to passing the center of the square area on which the thrombus-inducing material was applied was that the thrombus-inducing material dries from its periphery and the center dries finally, so that the surface of the center may not be smooth. As the collagen type I, one having a concentration of 3 mg/ml was used. As the PT reagent, one prepared by dissolving 1 vial of PT reagent manufactured by Sysmex Corporation in 2 ml of purified water and dialyzing the resulting solution against purified water overnight, followed by mixing the resultant at a ratio of 1:1 was used.

To the blood reservoir 433, the first pump 420 was connected, and the first connection nozzle 435 and the second connection nozzle 436 were connected to the second pump 421 and the third pump 422, respectively, via tubes.

Mineral oil was filled in the first pump 420; 0.2 M calcium chloride solution was filled in the second pump 421; and 0.5 M EDTA (pH 10) solution was filled in the third pump 422.

Blood was anticoagulated by mixing the blood immediately after collection with 3.2% sodium citrate solution at a volume ratio between the blood and the sodium citrate solution being 9:1 and adding a corn-derived trypsin inhibitor to the resulting mixture to a final concentration of 25 μg/ml, followed by filling the treated blood in the blood reservoir 433.

The programs for the first pump 420, second pump 421 and the third pump 422 are shown in Table 3 below. According to a program, the blood was injected to the microchip 4 and allowed to flow to the merged channel while being mixed with calcium chloride.

The data of changes in pressure measured by the pressure sensor 432 when the blood was allowed to flow to the merged channel are shown in FIG. 13 as (a).

TABLE 3

Programs for pumps

| Step No. | Time 0-6000 Seconds | First pump Blood reservoir Flow rate 0-10000 μL/min. | Third pump Second Connection Nozzle Flow rate 0-10000 μL/min. | Second pump First Connection Nozzle Flow rate 0-5000 μL/min. |
|---|---|---|---|---|
| 1 | 10 | 0.0 | 0.0 | 4.8 |
| 2 | 20 | 50.0 | 0.0 | 1.2 |
| 3 | 10 | 10.0 | 40.0 | 0.95 |
| 4 | 10 | 10.0 | 80.0 | 0.71 |
| 5 | 120 | 10.0 | 40.0 | 0.71 |
| 6 | 10 | 10.0 | 80.0 | 0.71 |
| 7 | 120 | 10.0 | 40.0 | 0.71 |
| 8 | 10 | 10.0 | 80.0 | 0.71 |

TABLE 3-continued

Programs for pumps

| Step No. | Time 0-6000 Seconds | First pump Blood reservoir Flow rate 0-10000 μL/min. | Third pump Second Connection Nozzle Flow rate 0-10000 μL/min. | Second pump First Connection Nozzle Flow rate 0-5000 μL/min. |
|---|---|---|---|---|
| 9 | 120 | 10.0 | 40.0 | 0.71 |
| 10 | 10 | 10.0 | 80.0 | 0.71 |
| 11 | 120 | 10.0 | 40.0 | 0.71 |
| 12 | 10 | 10.0 | 80.0 | 0.71 |
| 13 | 120 | 10.0 | 40.0 | 0.71 |
| 14 | 10 | 10.0 | 80.0 | 0.71 |
| 15 | 120 | 10.0 | 40.0 | 0.71 |
| 16 | 10 | 10.0 | 80.0 | 0.71 |
| 17 | 120 | 10.0 | 40.0 | 0.71 |
| 18 | 10 | 10.0 | 80.0 | 0.71 |
| 19 | 120 | 10.0 | 40.0 | 0.71 |
| 20 | 10 | 10.0 | 80.0 | 0.71 |
| 21 | 120 | 10.0 | 40.0 | 0.71 |
| 22 | 10 | 10.0 | 80.0 | 0.71 |
| 23 | 120 | 10.0 | 40.0 | 0.71 |
| 24 | 10 | 10.0 | 80.0 | 0.71 |
| 25 | 120 | 10.0 | 40.0 | 0.71 |
| 26 | 10 | 10.0 | 80.0 | 0.71 |
| 27 | 120 | 10.0 | 40.0 | 0.71 |
| 28 | 10 | 10.0 | 80.0 | 0.71 |
| 29 | 120 | 10.0 | 40.0 | 0.71 |
| 30 | 10 | 10.0 | 80.0 | 0.71 |
| 31 | 120 | 10.0 | 40.0 | 0.71 |
| 32 | 10 | 10.0 | 80.0 | 0.71 |
| 33 | 120 | 10.0 | 40.0 | 0.71 |
| 34 | 10 | 10.0 | 80.0 | 0.71 |
| 35 | 120 | 10.0 | 40.0 | 0.71 |
| 36 | 10 | 10.0 | 80.0 | 0.71 |
| 37 | 120 | 10.0 | 40.0 | 0.71 |
| 38 | 10 | 10.0 | 80.0 | 0.71 |
| 39 | 120 | 10.0 | 40.0 | 0.71 |
| 40 | 10 | 10.0 | 80.0 | 0.71 |
| 41 | 120 | 10.0 | 40.0 | 0.71 |
| 42 | 10 | 10.0 | 80.0 | 0.71 |
| 43 | 120 | 10.0 | 40.0 | 0.71 |
| 44 | 10 | 10.0 | 80.0 | 0.71 |
| 45 | 120 | 10.0 | 40.0 | 0.71 |
| 46 | 10 | 10.0 | 80.0 | 0.71 |
| 47 | 120 | 10.0 | 40.0 | 0.71 |
| 48 | 10 | 10.0 | 80.0 | 0.71 |
| 49 | 120 | 10.0 | 40.0 | 0.71 |
| 50 | 10 | 10.0 | 80.0 | 0.71 |

FIG. 14 shows an example wherein, in the present measurement example, a white thrombus was allowed to form and still images thereof were taken with time by the driven CCD camera 424 in FIG. 12, followed by reconstruction of the images. By taking pictures at a fixed position at constant intervals, a process wherein a white thrombus was gradually formed, leading to obstruction of the channel of the microchip 4 was observed.

Example 8

The microchip 4 in Example 7 was recovered from the thrombus monitoring device and the substrate 400 and the substrate 410 were peeled, followed by recovering the white thrombus formed on the thrombus-inducing material-placing section, which thrombus was constituted by coagulated blood and activated platelets. The recovered white thrombus were fixed with 1% glutaraldehyde and osmium tetroxide and dried by the critical point drying method, followed by observation with a scanning electron microscope. Further, whole blood coagulated by recalcification under a static condition was processed in the same manner and observed with a scanning electron microscope for comparison.

FIG. 15A is an electron micrograph showing a white thrombus formed in the microchip, and FIG. 15B is an electron micrograph showing a blood clot formed under a static condition.

In contrast to FIG. 15A wherein platelets are the main component and erythrocytes are hardly observed, FIG. 15B shows the blood clot formed with erythrocytes entangled with fibrin fibers. From the difference between A and B in FIG. 15, it can be seen, also in an analysis at the micro level, that a thrombus formed in the present thrombus monitoring device is different from a conventional blood clot formed by coagulation of whole blood in the absence of blood flow. Further, by peeling the microchip 4 and carrying out more detailed observations and analyses, more detailed information can be obtained.

Example 9

A measurement was carried out in the same manner as in Example 7 except that low-molecular-weight heparin (fragmin) was further added to blood to a final concentration of 0.5 U/ml.

An increase in pressure due to thrombus formation measured by the pressure sensor 432 is shown in FIG. 13(c).

Example 10

A measurement was carried out in the same manner as in Example 7 except that, instead of 0.2 M calcium chloride solution, 0.2 M calcium chloride solution containing 8,000 U/ml tPA reagent (Cleactor, Eisai Co., Ltd.) was filled in the second pump 421.

An increase in pressure due to thrombus formation measured by the pressure sensor 432 is shown in FIG. 13(b).

Example 11

An example of measurement of platelet function using the thrombus monitoring system C shown in FIG. 12 will now be shown.

All channels of the substrate 400 had a depth of 120 μm; the first channel 401 and the merged channel 403 had a width of 250 μm; the second channel 402 had a width of 50 μm; and the third channel 406 had a width of 50 μm. The first inlet 411 had a diameter of 2 mm; the second inlet 412 had a diameter of 0.7 mm; and the third inlet 418 had a diameter of 2 mm. The first connection nozzle 435 had an outer diameter of 0.7 mm; the second connection nozzle 436 had an outer diameter of 2 mm; and the outlet 414 had a diameter of 2 mm. The stirring section 413 was in the shape of a circle having a diameter of 1.5 mm and narrowing in fan-like fashion in the direction toward the downstream, and its depth was 1.2 mm. The stirring bar 417 was a stirring bar in the shape of a cylinder having a length of 2 mm and a diameter of 1 mm, whose surface was coated with nickel.

As the thrombus-inducing agent, 24 μL of a mixture of collagen type I (Nitta Gelatin Inc.) and PT reagent (Sysmex Corporation) was applied in a square shape sizing 1 cm×1 cm, and dried under reduced pressure at −0.08 MPa for 3 hours. The coating with the thrombus-inducing material was carried out such that the merged channel 403 was not passing the center of the square area on which the thrombus-inducing material was applied, that is, such that the merged channel 403 was passing 2.5 mm away from an edge of the square, when the substrate 400 and the substrate 410 were bonded to each other. As the collagen type I, one having a concentration of 3 mg/ml was used. As the PT reagent, one prepared by dissolving 1 vial of PT reagent manufactured by Sysmex Corporation in 2 ml of purified water and dialyzing the resulting solution against purified water overnight, followed by mixing the resultant at a ratio of 1:1 was used.

To the blood reservoir 433, the first pump 420 was connected, and the first connection nozzle 435 and the second connection nozzle 436 were connected to the second pump 421 and the third pump 422, respectively.

Mineral oil was filled in the first pump 420; purified water and 1 μM or 2 μM ADP solution were filled in the second pump 421; and 0.5 M EDTA (pH 10) solution was filled in the third pump 422.

Blood prepared by mixing the blood immediately after collection with 3.2% sodium citrate solution at a volume ratio between the blood and the sodium citrate solution being 9:1 was filled in the blood reservoir 433.

The programs executed for the first pump 420, second pump 421 and the third pump 422 were the same with those in Example 7 (Table 3).

In the case where purified water was filled in the second pump 421, no platelet clot was found even 30 minutes after the beginning of the measurement. In the case where 1 μM or 2 μM ADP was filled in the second pump 421, an obvious platelet aggregate was formed in the thrombus formation chamber 415 15 minutes or 10 minutes after the beginning of the measurement, respectively. However, since the strength of the platelet aggregate was low, no increase in pressure occurred.

The present invention was illustrated hereinbefore referring to the best embodiments, but the present invention is not restricted to these Examples and embodiments, and various modifications are possible as long as these are within the scope of the present invention.

For example, as the stirrer bar, a stirring bar consisting of a columnar projection described in Patent Literature 3, a stirring bar which vibrates by the piezoelectric effect described in Patent Literature 4, a stirring bar which rotates by light pressure described in Patent Literature 5, or the like can be used after being subjected to coagulation inhibition treatment.

INDUSTRIAL APPLICABILITY

The microchip, blood monitoring device and blood monitoring method of the present invention can be preferably employed for evaluation of the efficacy of an antithrombotic agent administered to a patient or the like and comprehensive monitoring of thrombus formation by blood coagulation and platelets under circumstances equivalent to those in the blood flow using a small amount of blood.

The invention claimed is:
1. A microchip comprising therein:
  a first channel which allows inflow of a first liquid selected from whole blood, platelet-rich plasma and a drug-treated liquid thereof;
  a second channel connected to the first channel, which allows inflow of a second liquid containing an agent that is reactive with said first liquid; and
  a merged channel extended from the connection portion of the first channel with the second channel,
  wherein, in said merged channel, a stirring section having a stirring bar for mixing said first liquid with said second liquid is provided, wherein the width of said stirring section gradually decreases in the direction toward the downstream, and the depth of said stirring section gradually decreases in the direction toward the downstream.

2. The microchip of claim 1, wherein the surface of said stirring bar has been subjected to coagulation inhibition treatment.

3. The microchip of claim 2, wherein said coagulation inhibition treatment is a treatment by which at least the surface of said stirring bar is formed with heparin, polyvinyl lactonamide or poly(2-methoxyethyl acrylate).

4. The microchip of claim 1, wherein the width of said stirring section is larger than that of said merged channel.

5. The microchip of claim 1, wherein the depth of said stirring section is larger than that of said merged channel.

6. The microchip of claim 1, wherein the depth of said merged channel is 50 μm to 200 μm.

7. The microchip of claim 1, wherein said microchip has been constituted by laminating a first substrate having a groove engraved on the surface, which groove constitutes said first channel, second channel and merged channel, and a second substrate having a hole engraved on the surface, which hole corresponds to said stirring section, such that the opening sections of said groove and hole are facing inward.

8. The microchip of claim 7, wherein the bonding strength between said first substrate and said second substrate is 0.5 to 50 kgf.

9. The microchip of claim 1, said microchip having, in the downstream of said stirring section, a thrombus formation chamber which has been provided with, in at least a part of the inside thereof, a thrombus formation-inducing material which induces formation of a thrombus.

10. The microchip of claim 9, wherein said thrombus formation-inducing material is collagen or a mixture of collagen and tissue factor.

* * * * *